United States Patent
Ku et al.

(10) Patent No.: US 8,264,245 B2
(45) Date of Patent: Sep. 11, 2012

(54) DEVICE AND SYSTEM FOR MEASURING PROPERTIES OF CELLS AND METHOD OF MEASURING PROPERTIES OF CELLS USING THE SAME

(75) Inventors: Bo Sung Ku, Gyunggi-do (KR); Tae Yoon Kim, Seoul (KR); Young-Ho Cho, Daejeon (KR); Young Soo Oh, Gyunggi-do (KR); Sung Koo Kang, Gyunggi-do (KR); Sang Jin Kim, Gyunggi-do (KR)

(73) Assignee: Samsung Electro-Mechanics Co., Ltd., Suwon, Gyunggi-Do (KR)

( * ) Notice: Subject to any disclaimer, the term of this patent is extended or adjusted under 35 U.S.C. 154(b) by 420 days.

(21) Appl. No.: 12/544,098

(22) Filed: Aug. 19, 2009

(65) Prior Publication Data

US 2010/0321045 A1 Dec. 23, 2010

(30) Foreign Application Priority Data

Jun. 18, 2009 (KR) ................. 10-2009-0054405

(51) Int. Cl.
*G01R 27/08* (2006.01)
(52) U.S. Cl. ........................................ 324/692
(58) Field of Classification Search .................. None
See application file for complete search history.

(56) References Cited

U.S. PATENT DOCUMENTS

| | | | |
|---|---|---|---|
| 4,863,226 A | 9/1989 | Houpt et al. | |
| 5,022,743 A | 6/1991 | Kino et al. | |
| 5,032,720 A | 7/1991 | White | |
| 5,836,200 A * | 11/1998 | Belonenko et al. | 73/61.79 |
| 2004/0209351 A1 | 10/2004 | Thielecke et al. | |
| 2005/0212095 A1* | 9/2005 | Vestergaard et al. | 257/646 |
| 2006/0199173 A1 | 9/2006 | Thielecke et al. | |
| 2007/0182417 A1* | 8/2007 | Giaever et al. | 324/426 |
| 2010/0136606 A1* | 6/2010 | Katsumoto et al. | 435/29 |

* cited by examiner

*Primary Examiner* — Jermele M Hollington
(74) *Attorney, Agent, or Firm* — Blakely Sokoloff Taylor & Zafman LLP

(57) ABSTRACT

According to a device and system for measuring the properties of cells, there is an advantage in that, since a cell accommodation unit having a volume is provided, the properties of three-dimensional cells can be measured. Further, the present invention is advantageous in that it enables passive measurement of multiple properties which passively measures the electrical, mechanical and/or optical properties of cells, and active measurement of multiple properties which actively applies electrical, mechanical and optical types of stimulation to cells and measures their electrical, mechanical and/or optical reactions, thus measuring the multiple properties of cells with high reliability.

22 Claims, 22 Drawing Sheets

DEVICE AND SYSTEM FOR MEASURING PROPERTIES OF CELLS AND METHOD OF MEASURING PROPERTIES OF CELLS USING THE SAME

CROSS REFERENCE TO RELATED APPLICATION(S)

This application claims the benefit of Korean Patent Application No. 10-2009-0054405, filed on Jun. 18, 2009, entitled "Device and System for Measuring Properties of Cells and Method of Measuring Properties of Cells Using the Same", which is hereby incorporated by reference in its entirety into this application.

BACKGROUND OF THE INVENTION

1. Technical Field

The present invention relates to a device and method for measuring the properties of cells.

2. Description of the Related Art

The present invention relates generally to a device and method for measuring the properties of cells, and, more particularly, to a device for measuring the properties of cells, which analyzes multiple properties including the electrical properties containing the impedance of cells, mechanical properties containing deformability, stiffness, etc., and/or optical properties containing size, fluorescence, etc., thus analyzing the properties of the cells with high reliability. Further, through the use of the device for measuring the properties of cells according to the present invention, electrical stimulation including voltage, mechanical stimulation including pressure, and/or optical stimulation including light is applied to cells, and the reactions of the cells to the stimulation are analyzed, and thus multiple properties of the cells can be actively analyzed.

Generally, analyzing the physical properties of cells is an action which is widely performed for the diagnosis of disease or the examination of drug effects or toxicity. In particular, in order to analyze the effects of an anticancer drug, an optical method of cultivating cancer cells in the form of a two-dimensional monolayer using an in-vitro method, processing the anticancer drug and analyzing the fluorescence of cells has been mainly performed. However, since such a two-dimensional monolayer cancer cell cannot reflect the properties of actual three-dimensional cancer tissue in the human body, it is difficult to apply information about the effects of the anticancer drug, obtained from the two-dimensional monolayer cancer cell, to clinical conditions within a human body (in-vivo method) without change. Therefore, there is a need to culture cancer cells in a three-dimensional form which is similar to three-dimensional cancer tissue within an actual human body (in-vivo like environment), and analyze the effects of an anticancer drug. Accordingly, a cell property measurement device capable of effectively analyzing the properties of cells clustered in three dimensions is required. Furthermore, in order to improve the reliability of property analysis, a method capable of collectively measuring multiple properties including optical, electrical and/or mechanical properties is also required in addition to the conventional optical measurement method.

In order to measure the properties of these three-dimensional cells, only one of an optical method and an electrical method has been used in conventional technology. First, conventional methods of measuring the optical properties of three-dimensional cells are those which process a fluorescent probe on three-dimensional cells and measure a fluorescence image using a confocal microscope. The confocal microscope is disclosed in U.S. Pat. Nos. 4,863,226, 5,022,743, 5,032,720, etc. However, this method entails a long measurement time, makes long-term real-time measurement impossible due to the influence of the photo-bleaching of the fluorescent probe, and influences the activity of cells due to the biochemical influence of the fluorescent probe. As a result, it is difficult to measure the properties of cells while maintaining the activity of the cells for a long period of time. Further, such a method has limited reliability because it can measure only the optical properties of cells rather than multiple properties of the cells.

Further, conventional methods of measuring the electrical properties of three-dimensional cells are those which install electrodes around three-dimensional cells, or provide an orifice through which three-dimensional cells pass and install electrodes on both sides of the orifice, thus measuring electrical properties such as impedance of three-dimensional cells. These methods are disclosed in U.S. Patent Publication Nos. 2004-0209351 and 2006-0199173. However, since these methods use a well having the same size as a three-dimensional cell or an orifice having a size smaller than the three-dimensional cell, the space in which cells can be cultured and proliferated is not present, and thus it is difficult to measure the properties of a three-dimensional cell while culturing and maintaining the three-dimensional cell for a long period of time. Further, since such a method can measure only the electrical properties of cells rather than multiple properties, reliability of measurement is limited.

SUMMARY OF THE INVENTION

Accordingly, the present invention has been made keeping in mind the above problems occurring in the prior art, and the present invention is intended to provide the structures of a device and system for measuring the properties of cells and a method of measuring the properties of cells, which can measure multiple properties including the electrical, mechanical and/or optical properties of cells clustered in three dimensions.

In accordance with an aspect of the present invention, there is provided a device for measuring properties of cells, comprising a well including a cell accommodation unit connected to an inlet and an outlet, and a first electrode accommodation unit and a second electrode accommodation unit arranged with the cell accommodation unit disposed therebetween; an electrical property measurement unit including a first electrode formed in the first electrode accommodation unit and a second electrode formed in the second electrode accommodation unit so as to measure electrical properties of cells accommodated in the cell accommodation unit and/or apply electrical stimulation to the cells; and electric field connection channels formed between the first electrode accommodation unit and the cell accommodation unit and between the second electrode accommodation unit and the cell accommodation unit, and configured to control a pattern of electric fields in the cell accommodation unit in three dimensions by adjusting angles of the electric field connection channels.

Preferably, the well further includes a mechanical property measurement unit arranged either above or below or both above and below the cell accommodation unit and configured to measure mechanical properties of the cells and/or to apply mechanical stimulation to the cells.

Preferably, the first electrode and the second electrode are arranged symmetrically or asymmetrically with respect to the cell accommodation unit.

Preferably, the first electrode includes a plurality of first electrode units and the second electrode includes a plurality of second electrode units.

Preferably, each of the first electrode and the second electrode has a polygonal shape or an arc shape.

Preferably, the device further comprises a ground electrode formed in the cell accommodation unit.

Preferably, each of the first electrode accommodation unit and the second electrode accommodation unit includes a plurality of divided spaces.

Preferably, the mechanical property measurement unit includes a membrane actuating channel formed either above or below or both above and below the cell accommodation unit of the well and a membrane arranged between the membrane actuating channel and the cell accommodation unit so as to isolate the membrane actuating channel from the cell accommodation unit, and the membrane is made of an elastically deformable material.

Preferably, the device further comprises an optical property measurement unit arranged outside the well or arranged in the cell accommodation unit of the well and configured to measure optical properties of the cells and/or to apply optical stimulation to the cells.

Preferably, the membrane includes a plurality of membrane units that are independently or dependently actuated.

Preferably, the device further comprises a circuit unit arranged outside the well and configured to control the electrical property measurement unit, the mechanical property measurement unit and the optical property measurement unit and to measure properties of the cells accommodated in the cell accommodation unit according to signals detected by the electrical property measurement unit, the mechanical property measurement unit and the optical property measurement unit.

Preferably, the membrane is made of a gas- or liquid-permeable material.

In accordance with another aspect of the present invention, there is provided a system for measuring properties of cells, wherein a plurality of devices for measuring properties of cells is connected in series or parallel, or through a combination of series and parallel connections.

Preferably, inlets of the cell property measurement devices are connected in parallel.

Preferably, an outlet of any one of the cell property measurement devices is connected in series with an inlet of another cell property measurement device.

Preferably, first electrodes or second electrodes of the cell property measurement devices are connected in a matrix connective shape or an individual connective shape.

In accordance with a further aspect of the present invention, there is provided a method of measuring properties of cells, comprising (A) providing a device for measuring properties of cells, the device including a cell accommodation unit connected to an inlet and an outlet and configured to accommodate cells and have a volume, an electrical property measurement unit, a mechanical property measurement unit, and/or an optical property measurement unit; (B) supplying cells into the cell accommodation unit of the cell property measurement device; and (C) collectively measuring mechanical, electrical and/or optical properties of the cells.

Preferably, the method further comprises, before (C), applying mechanical stimulation, electrical stimulation, optical stimulation or a combination thereof to the cells accommodated in the cell accommodation unit.

Preferably, the electrical stimulation is Direct Current (DC) stimulation, Alternating Current (AC) stimulation, or a combination thereof, the mechanical stimulation is static or dynamic stimulation, and the optical stimulation is static or dynamic stimulation.

Preferably, the electrical properties include resistance, capacitance or impedance, the mechanical properties include stiffness, deformability or a Poisson ratio, and the optical properties include fluorescence, luminescence, absorbance, number, or size.

Preferably, the electrical property measurement unit is a component including a first electrode formed in a first electrode accommodation unit and a second electrode formed in a second electrode accommodation unit so as to measure electrical properties of the cells accommodated in the cell accommodation unit and/or to apply electrical stimulation to the cells, the first electrode includes a plurality of first electrode units and the second electrode includes a plurality of second electrode units, and the electrical stimulation is applied in common to the first electrode or the second electrode, or individually applied to the first electrode units or the second electrode units.

Preferably, the mechanical property measurement unit includes a membrane actuating channel formed either above or below or both above and below the cell accommodation unit and a membrane disposed between the membrane actuating channel and the cell accommodation unit so as to isolate the membrane actuating channel from the cell accommodation unit, the membrane includes a plurality of membrane units that are independently or dependently actuated, and the mechanical stimulation is common membrane stimulation applied to the entire membrane, individual membrane stimulation individually applied to respective membrane units, or a combination thereof.

Preferably, the mechanical stimulation is applied in such a way as to elastically deform the membrane by adjusting an internal pressure of the membrane actuating channel.

Preferably, a gas required to create an environment for culturing the cells is injected into the cell accommodation unit through the membrane.

The features and advantages of the present invention will be more clearly understood from the following detailed description taken in conjunction with the accompanying drawings.

Furthermore, the terms and words used in the present specification and claims should not be interpreted as being limited to typical meanings or dictionary definitions, but should be interpreted as having meanings and concepts relevant to the technical scope of the present invention based on the rule according to which an inventor can appropriately define the concept implied by the term to best describe the method he or she knows for carrying out the invention.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
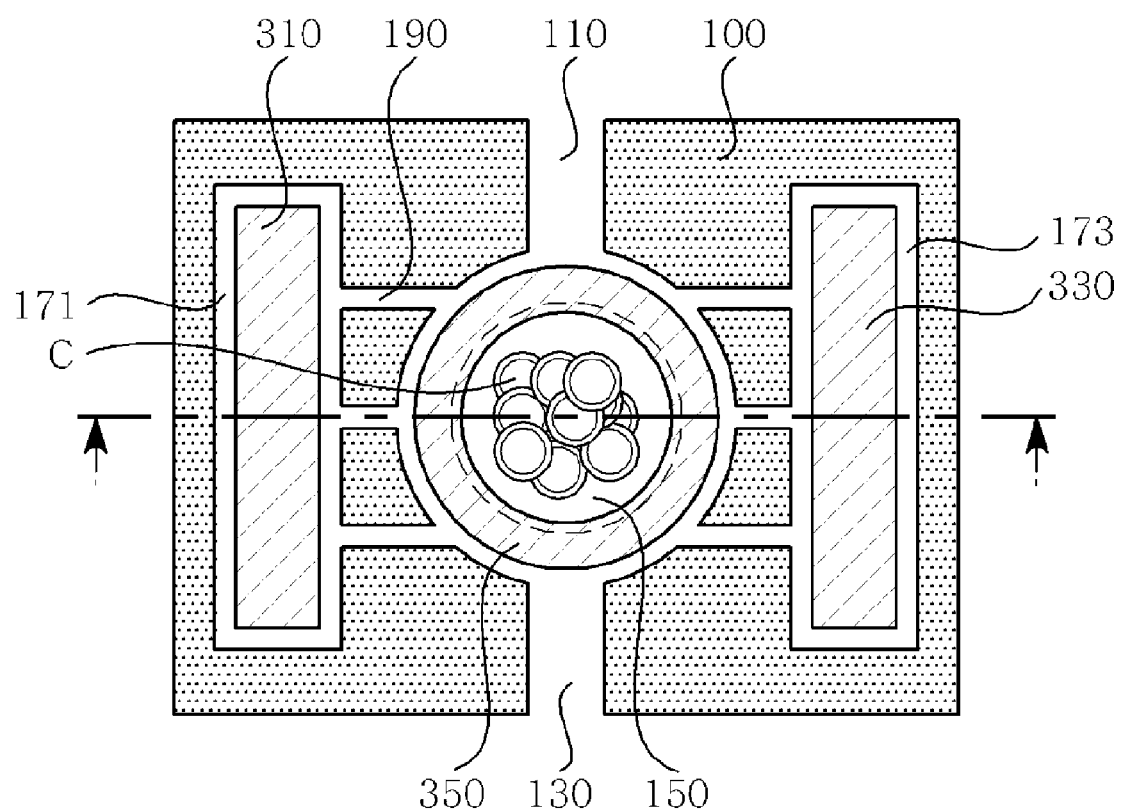
FIG. 1 is a plan view of a device for measuring the properties of cells according to an embodiment of the present invention.

Hereinafter, embodiments of a device and system for measuring the properties of cells and a method of measuring the properties of cells using the device and system according to the present invention will be described in detail with reference to the attached drawings. Reference now should be made to the drawings, in which the same reference numerals are used throughout the different drawings to designate the same or similar components, and a repeated description is omitted. In the present specification, the terms 'upper' and 'lower' are used to discriminate one component from another component, and these components are not limited by the above terms.

Figure 2:
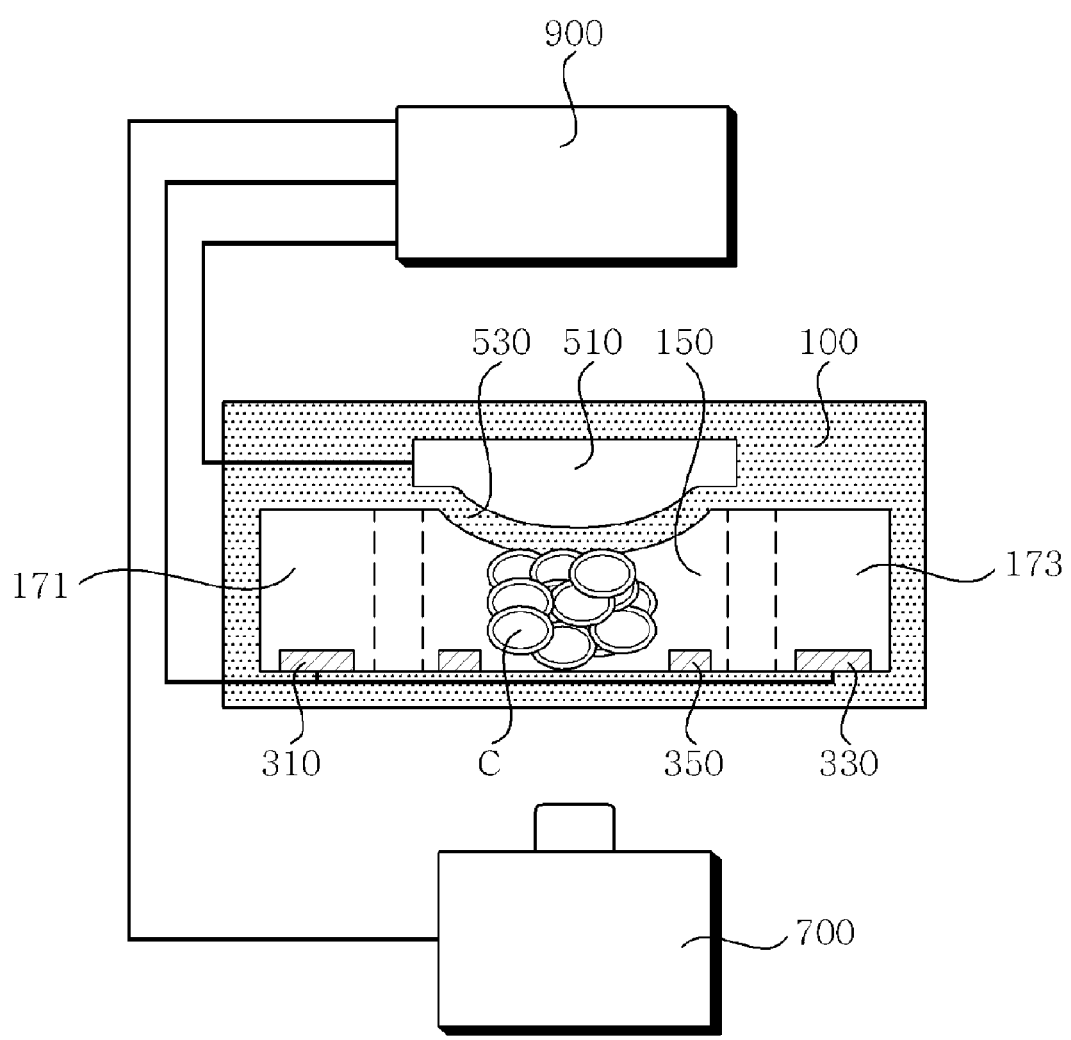
FIG. 2 is a sectional view of the cell property measurement device of FIG. 1 taken along a cutting line.

FIG. 1 is a plan view of a device for measuring the properties of cells according to an embodiment of the present invention, and FIG. 2 is a sectional view of the cell property measurement device of FIG. 1 taken along a cutting line.

As shown in FIG. 1, the cell property measurement device according to the present embodiment includes a well 100 including a cell accommodation unit 150 and electrode accommodation units 171 and 173, and electrodes 310 and 330 formed in the electrode accommodation units 171 and 173, respectively, to measure the electrical properties of cells accommodated in the cell accommodation unit 150 and/or to apply electrical stimulation to the cells.

The well 100 is an external structure in which the electrode accommodation units 171 and 173 and the cell accommodation unit 150, having an inlet 110 and an outlet 130, are provided. The well 100 may be a structure implemented as a single body, but may be a structure in which a separate cell accommodation unit 150 is combined with electrode accommodation units 171 and 173.

Such a well 100 is made of a biocompatible material, for example, polydimethylsiloxane (PDMS), polymethylmethacrylate (PMMA), biocompatible plastic material, a glass-series material, etc., but is not limited to the above examples. Preferably, a surface-treated layer for preventing cells from being fixed or a protein surface-treated layer for fixing the cells is formed on the surface of the well 100.

In this case, the cell accommodation unit 150 is a three-dimensional space formed in the well 100, and an area in which cells, that is, measurement targets, are located. The cell accommodation unit 150 is connected both to the inlet 110 and to the outlet 130 communicating with the outside of the well 100. The inlet 110 and the outlet 130 provide a path through which cells, a culture fluid, etc. can flow into or out of the cell accommodation unit 150. For example, the inlet 110 and the outlet 130 may be holes formed in the well 100, or alternatively, may include hollow pipes extending outwards from the well 100.

Figure 3:
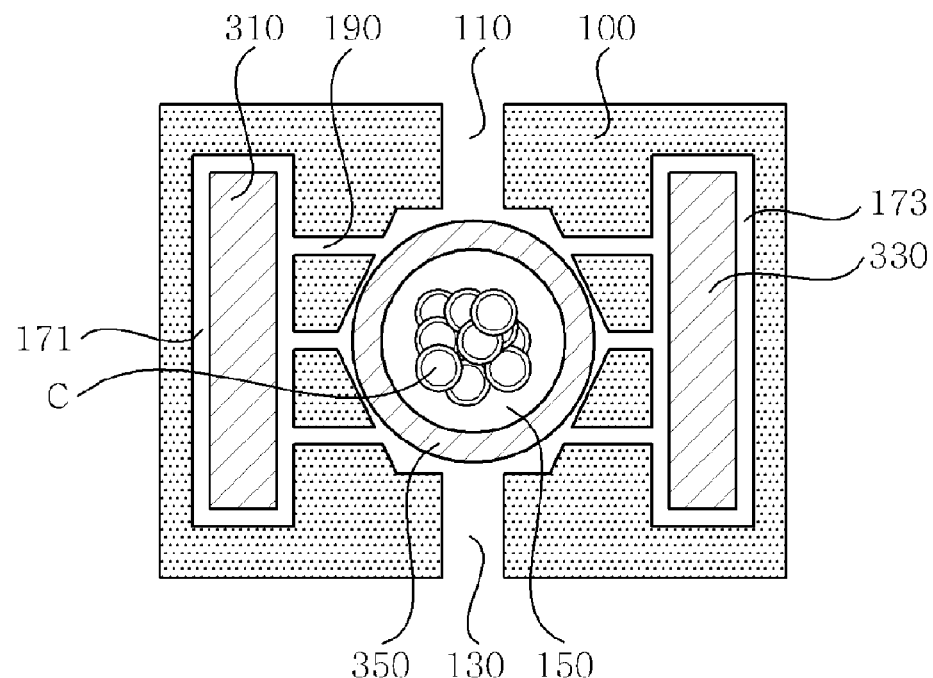
FIG. 3 is a plan view of a cell property measurement device having a circular cell accommodating unit.

The shape of the cell accommodation unit 150 is not particularly limited. The cell accommodation unit 150 may be formed in a circular shape, as shown in FIG. 1, or a polygonal shape, as shown in FIG. 3.

In this case, the electrode accommodation units 171 and 173 are spaces provided inside the well 100 so that the electrodes 310 and 330 for measuring the electrical properties of the cells and/or applying electrical stimulation to the cells are arranged. The well 100 includes at least two electrode accommodation units 171 and 173, that is, the first electrode accommodation unit 171 and the second electrode accommodation unit 173 arranged with the cell accommodation unit 150 disposed therebetween.

Figure 5:
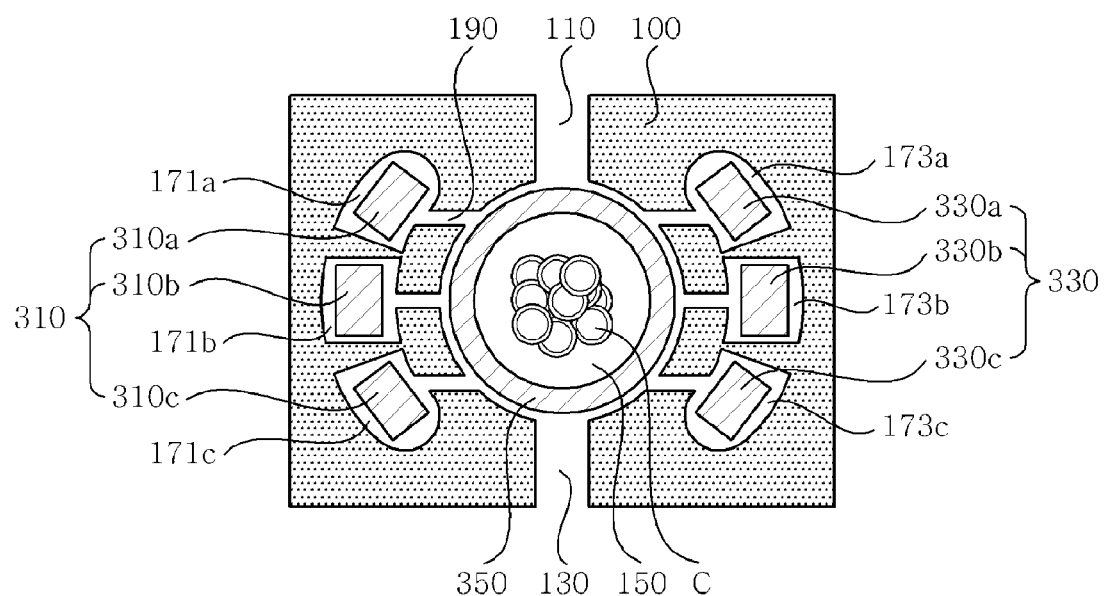
FIG. 5 is a plan view of a cell property measurement device having first and second electrode accommodation units, each being composed of a plurality of divided spaces.

The electrode accommodation units 171 and 173 do not need to be formed in space especially distinguished from the cell accommodation unit 150, but partition walls on which electric field connection channels 190 are formed are preferably present between the electrode accommodation units 171 and 173 and the cell accommodation unit 150. That is, the electric field connection channels 190 are formed between the first electrode accommodation unit 171 and the cell accommodation unit 150 and between the second electrode accommodation unit 173 and the cell accommodation unit 150. Each connection channel 190 may be an aggregate of a plurality of channels 190a, 190b and 190c. It is possible to apply uniform electric fields to the cell accommodation unit 150 through the electric field connection channels 190, and it is also possible to control the pattern of electric fields in the cell accommodation unit in three dimensions by adjusting the angles of the electric field connection channels 190. It can be seen that the direction of the electric field connection channels 190 of FIG. 5 is partially different from that of the electric field connection channels 190 of FIG. 27, and the angles of the electric field connection channels 190 can be adjusted using a variety of methods.

Figure 4:
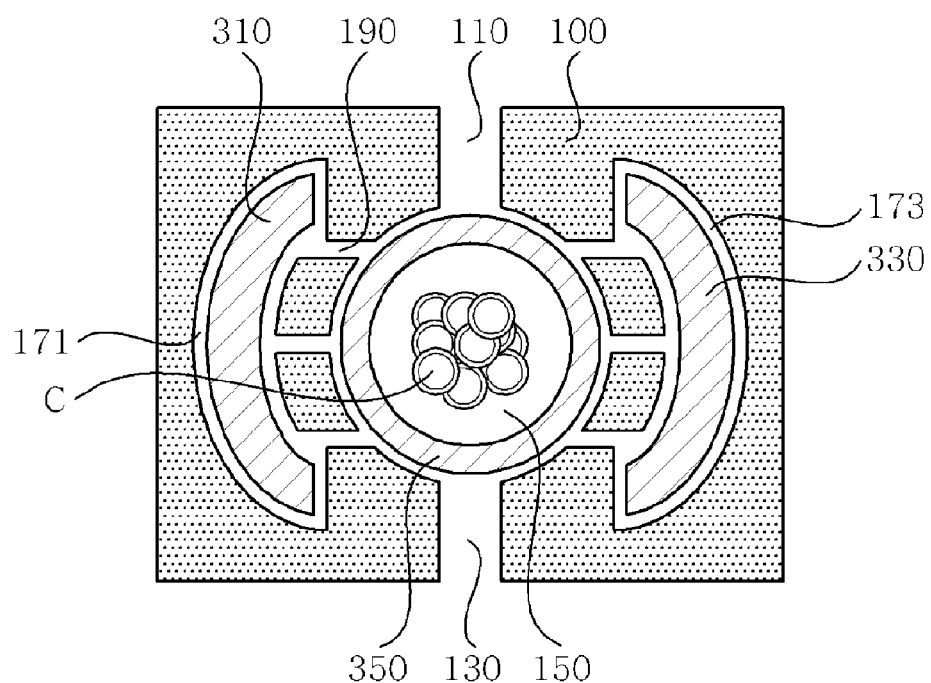
FIG. 4 is a plan view of a cell property measurement device having arc-shaped first and second electrodes.

The shape of the electrode accommodation units 171 and 173 is not particularly limited. As shown in FIG. 4, the electrode accommodation units 171 and 173 may be formed in an arc shape. Further, as shown in FIG. 5, each of the first and second electrode accommodation units 171 and 173 may be composed of a plurality of divided spaces. Here, FIG. 5 shows that the first electrode accommodation unit 171 is divided into three spaces 171a, 171b and 171c, and the second electrode accommodation unit 173 is divided into three spaces 173a, 173b and 173c.

The electrical property measurement unit is a component for measuring the electrical properties of the cells accommodated in the cell accommodation unit 150 and/or applying electrical stimulation to the cells. The cell property measurement device according to the present embodiment includes the first electrode 310 formed in the first electrode accommodation unit 171 and the second electrode 330 formed in the second electrode accommodation unit 173. Preferably, the first and second electrodes 310 and 330 are made of electric conductive metal such as gold, silver, copper, and nickel.

The shape of the first and second electrodes 310 and 330 is not particularly limited. Each of the first and second electrodes 310 and 330 may have a polygonal shape, as shown in FIG. 1, or an arc shape, as shown in FIG. 4.

Figure 6:
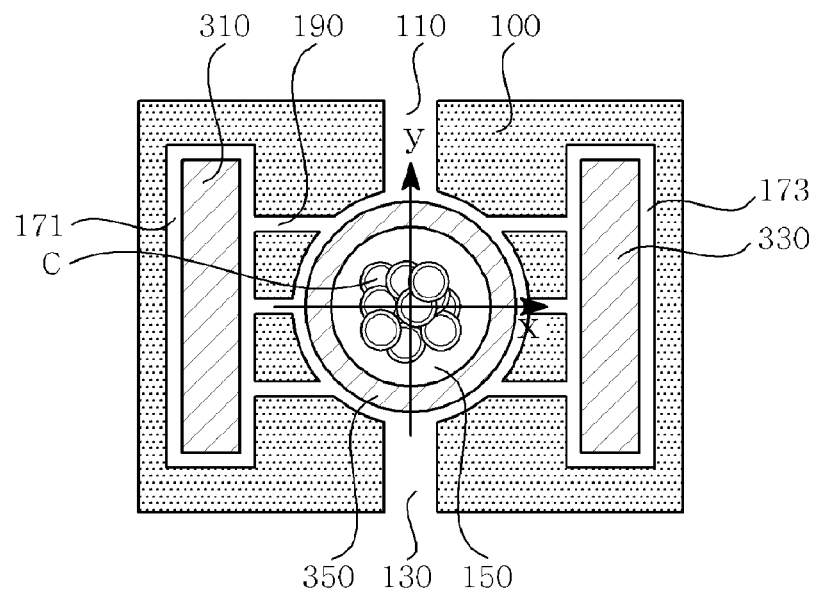
FIG. 6 is a plan view of a cell property measurement device in which first and second electrodes are arranged symmetrically with respect to x and y axes on the plan view.
Figure 7:
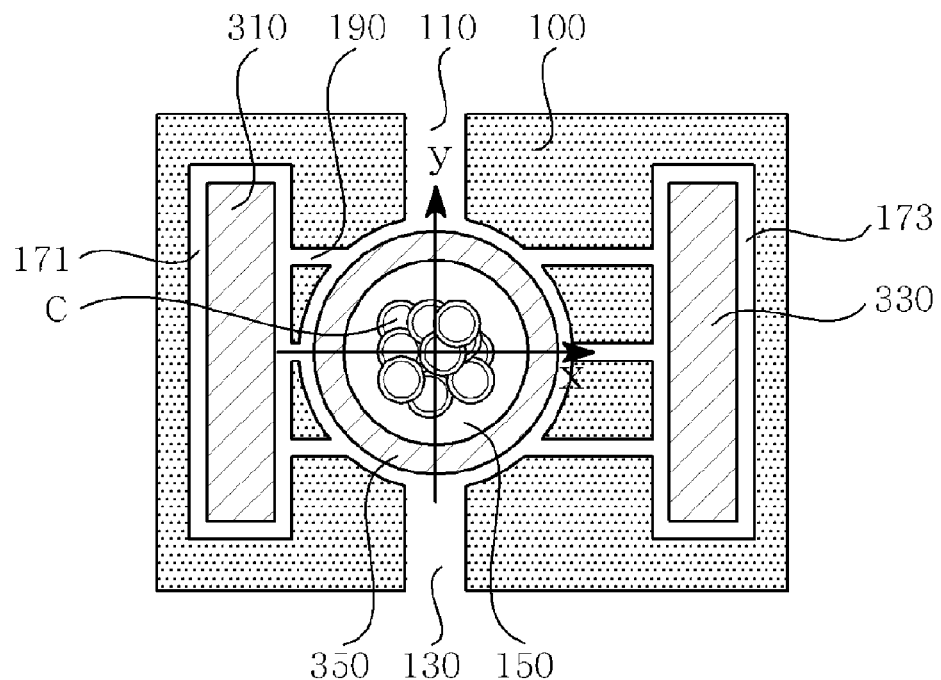
FIG. 7 is a plan view of a cell property measurement device in which first and second electrodes are arranged symmetrically with respect to an x axis, but asymmetrically with respect to a y axis on the plan view.
Figure 8:
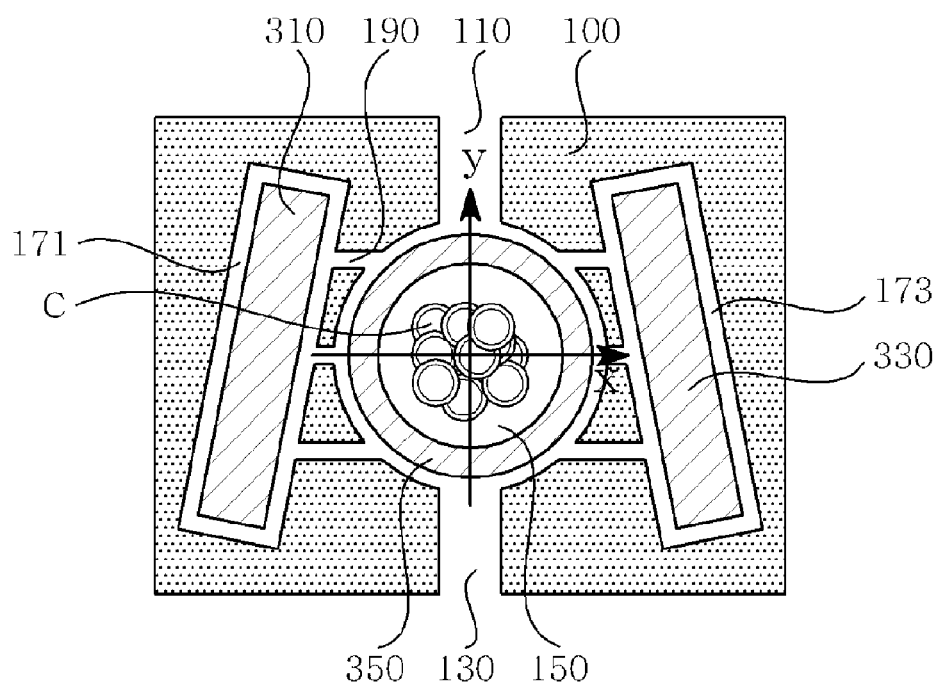
FIG. 8 is a plan view of a cell property measurement device in which first and second electrodes are arranged asymmetrically with respect to an x axis, but symmetrically with respect to a y axis on the plan view.
Figure 9:
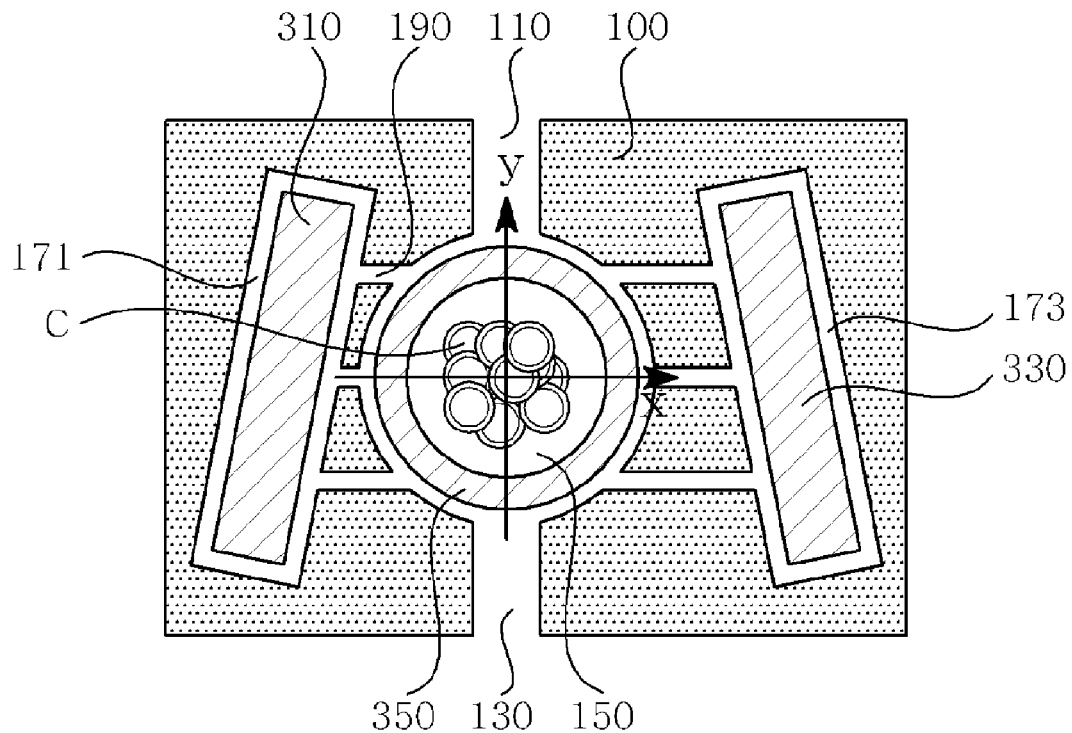
FIG. 9 is a plan view of a cell property measurement device in which first and second electrodes are arranged asymmetrically with respect to x and y axes on the plan view.

Further, the arrangement of the first electrode 310 and the second electrode 330 is not limited. The first and second electrodes 310 and 330 may be arranged symmetrically or asymmetrically with respect to the cell accommodation unit 150. That is, the first and second electrodes 310 and 330 may be arranged symmetrically with respect to x and y axes on the plan view, as shown in FIG. 6, may be arranged symmetrically with respect to the x axis, but asymmetrically with respect to the y axis, as shown in FIG. 7, may be arranged asymmetrically with respect to the X axis, but symmetrically with respect to the y axis, as shown in FIG. 8, or may be arranged asymmetrically with respect to the x and y axes, as shown in FIG. 9.

Figure 10:
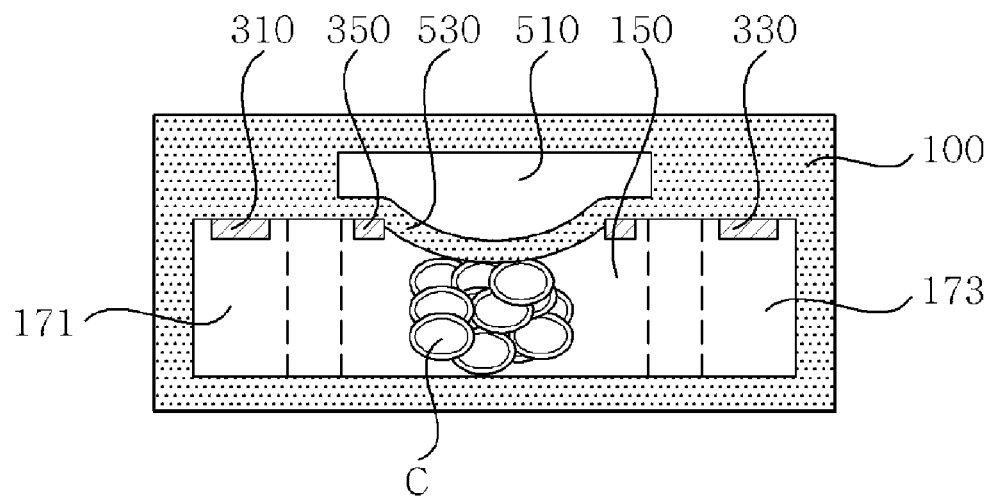
FIG. 10 is a sectional view of a cell property measurement device in which a first electrode, a second electrode and a ground electrode are formed in the upper portions of electrode accommodation units.
Figure 11:
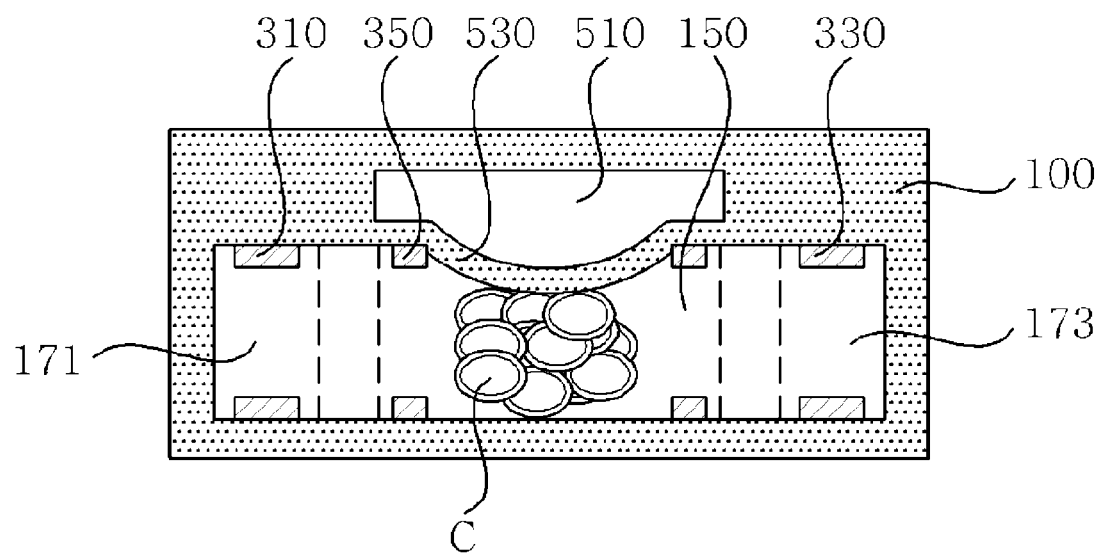
FIG. 11 is a sectional view of a cell property measurement device in which a first electrode, a second electrode and a ground electrode are formed in the upper and lower portions of electrode accommodation units.
Figure 12:
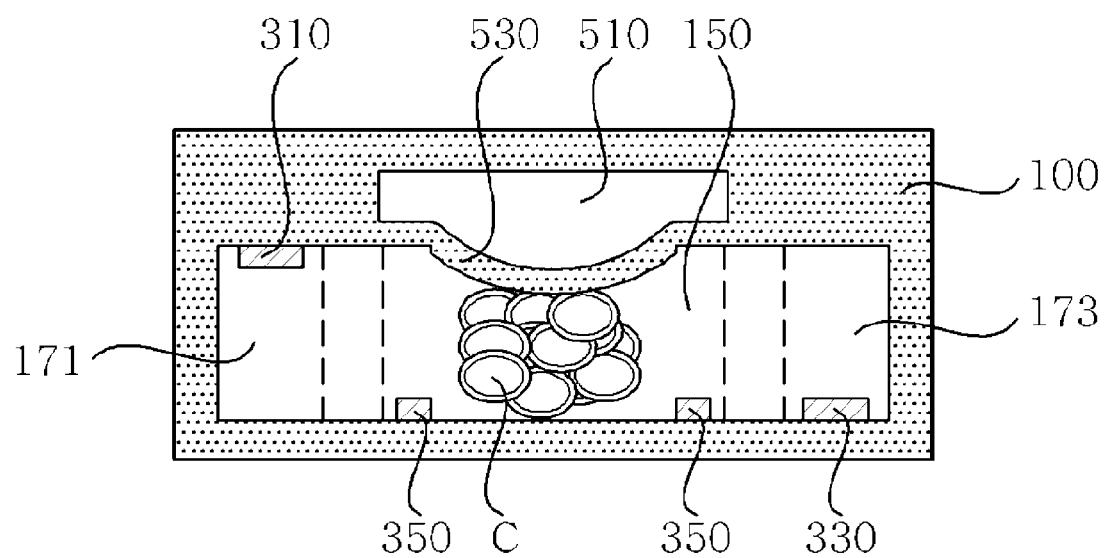
FIG. 12 is a sectional view of a cell property measurement device in which a first electrode is formed in the upper portion of a first electrode accommodation unit and a second electrode is asymmetrically formed in the lower portion of a second electrode accommodation unit.

Even on the sectional view, the first electrode 310 and the second electrode 330 may be formed in the lower portions of the electrode accommodation units 171 and 173, as shown in FIG. 2, may be formed in the upper portions of the electrode accommodation units 171 and 173, as shown in FIG. 10, may be formed in the upper and lower portions of the electrode accommodation units 171 and 173, as shown in FIG. 11, or may be asymmetrically formed, as shown in FIG. 12 in such a way that the first electrode 310 is formed in the upper portion of the first electrode accommodation unit 171 and the second electrode 330 is formed in the lower portion of the second electrode accommodation unit 173.

Figure 13:
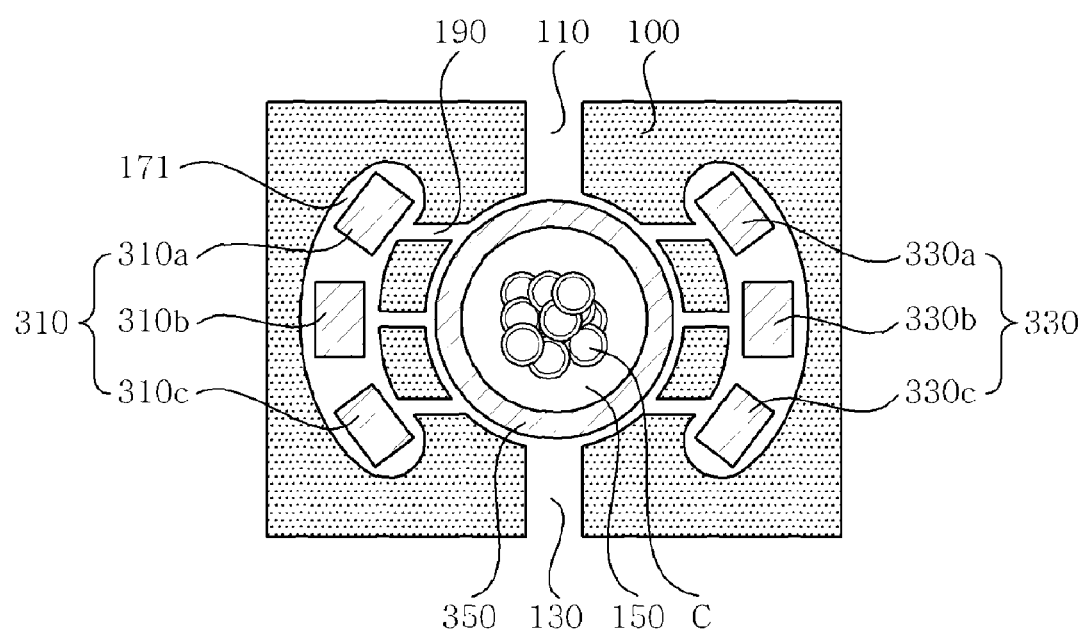
FIG. 13 is a plan view of a cell property measurement device in which a first electrode is composed of a plurality of first electrode units and a second electrode is composed of a plurality of second electrode units.

Each of the above-described first and second electrodes 310 and 330 may be a single body, but may be implemented as an aggregate of a plurality of electrode units. That is, as shown in FIG. 13, the first electrode 310 may be composed of a plurality of first electrode units 310a, 310b and 310c, and the second electrode 330 may be composed of a plurality of second electrode units 330a, 330b and 330c. At this time, when each of the first and second electrode accommodation units 171 and 173 is implemented as a plurality of divided spaces, as shown in FIG. 5, the first electrode units 310a, 310b and 310c and the second electrode units 330a, 330b and 330c may also be arranged in respective divided spaces.

Meanwhile, a ground electrode 350 is preferably formed in the cell accommodation unit 150. The ground electrode 350 is preferably formed in the shape of a closed curve enclosing the cell accommodation unit 150, for example, a circular or polygonal shape. Such a ground electrode 350 may be arranged in either or both of the upper portion and lower portion of the cell accommodation unit 150.

The above-described cell property measurement device may further include a mechanical property measurement unit arranged either above or below or both above and below the cell accommodation unit 150 and configured to measure the mechanical properties of the cells and/or to apply mechanical stimulation to the cells.

The mechanical property measurement unit may include a membrane actuating channel 510 formed either above or below or both above and below the cell accommodation unit 150 of the well 100, and a membrane 530 disposed between the membrane actuating channel 510 and the cell accommodation unit 150 so as to isolate the membrane actuating channel 510 from the cell accommodation unit 150.

The membrane actuating channel 510 is formed in the shape of a hollow either above or below or both above and below the cell accommodation unit 150 of the well 100, and is connected to a membrane actuation control unit (not shown). As will be described later, the membrane actuating channel 510 is a factor for determining the shape of the membrane 530 to be actuated.

The membrane 530 is a component made of an elastically deformable material and configured to apply mechanical stimulation to the cells and/or measuring the mechanical properties of the cells while the shape thereof is changed. In FIG. 2, for convenience of drawings, an example in which the membrane 530 and the well 100 are integrated into a single body, is shown, but the membrane 530 and the well 100 may be separate components. The membrane 530 may be an elastomeric membrane (or a deformable membrane) made of, for example, PDMS, natural rubber or synthetic polymer latex, soft or hard rubber, or a plastic material, and may be preferably made of a gas- or fluid-permeable material to create an environment for culturing the cells of the cell accommodation unit 150.

A method of deforming the membrane 530 is not particularly limited, and may be implemented using one of hydraulic, pneumatic, piezoelectric actuating, thermal actuating, electrostatic actuating and electromagnetic actuating methods. In the present embodiment, the pneumatic deformation method is used as the membrane deformation method. That is, when a gas is injected into the membrane actuating channel 510, the internal pressure of the membrane actuating channel 510 increases, and thus the membrane 530 elastically expands. As the membrane 530 elastically expands, mechanical stimulation is applied to the cells accommodated in the cell accommodation unit 150 in such a way as to apply pressure to the cells. In contrast, the motion of the membrane 530 attributable to the behavior of the cells is detected, and thus the mechanical properties of the cells can be measured. The amount that the membrane 530 is deformed can be controlled by adjusting the thickness of the membrane 530 or the cross-section and width of the membrane actuating channel 510.

Figure 14:
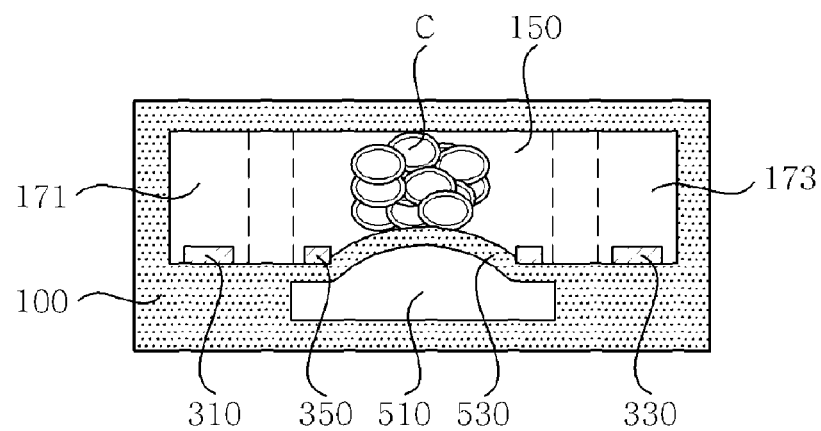
FIG. 14 is a sectional view of a cell property measurement device in which a membrane and a membrane actuating channel are formed in the lower portion of a well.
Figure 15:
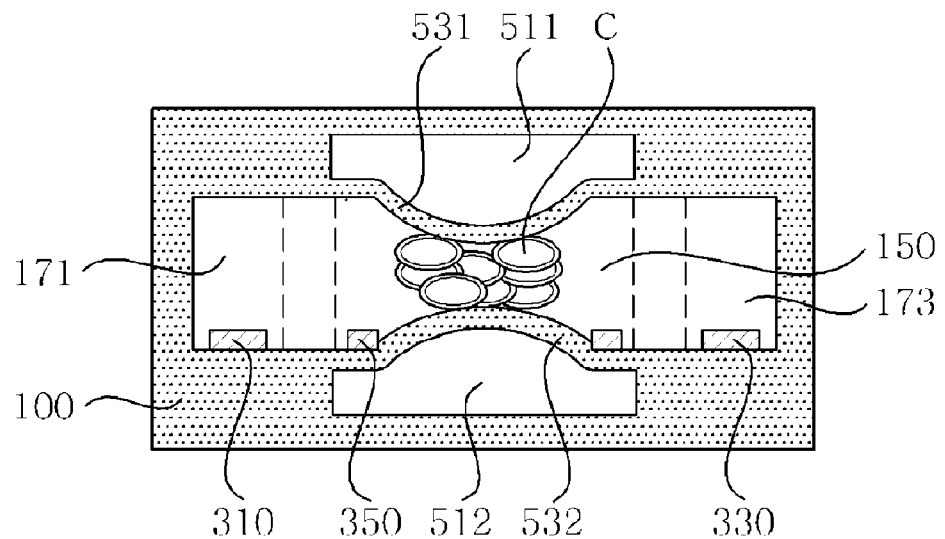
FIG. 15 is a sectional view of a cell property measurement device in which a membrane and a membrane actuating channel are formed in the upper and lower portions of a well.

In the above embodiment, a structure in which one membrane actuating channel 510 is formed in the upper portion of the well 100 has been described, but both the membrane 530 and the membrane actuating channel 510 may be formed in the lower portion of the well 100, as shown in FIG. 14, or in the upper and lower portions of the well 100, as shown in FIG. 15.

Figure 16:
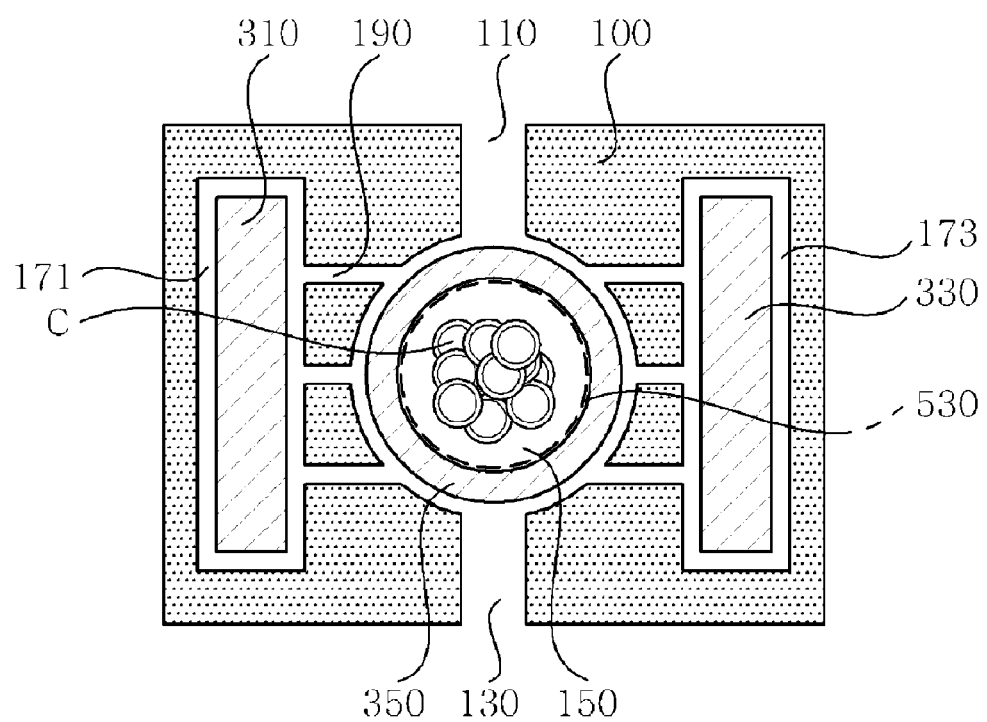
FIGS. 16 to 21 are views showing various embodiments of shape and arrangement of a membrane.
Figure 17:
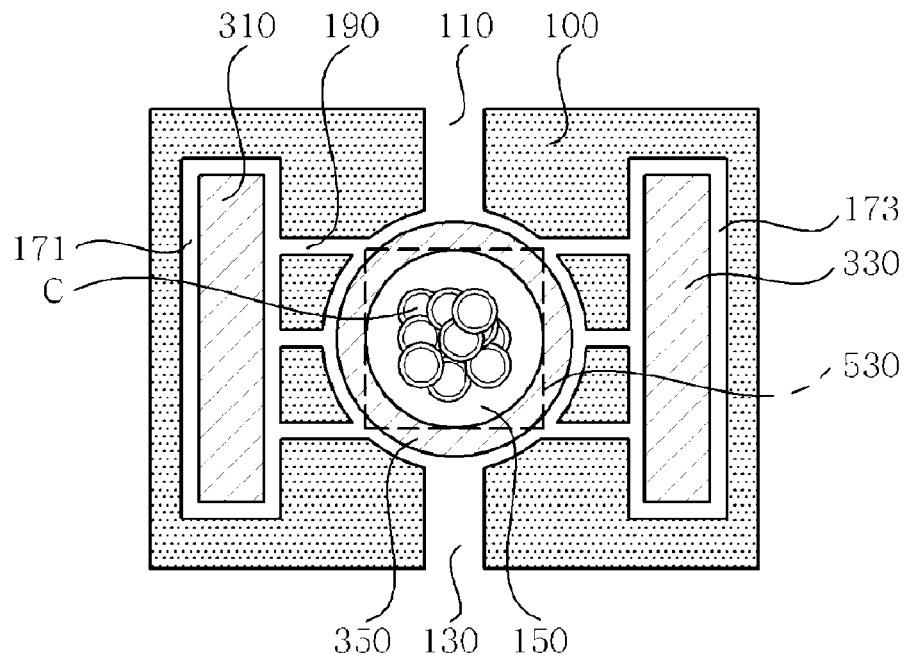
Figure 18:
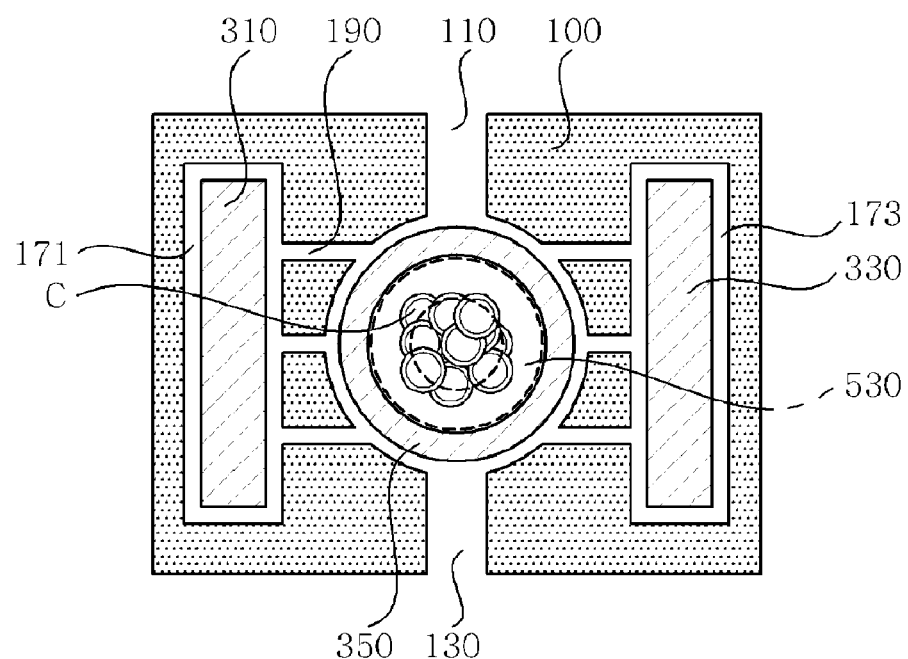
Figure 19:
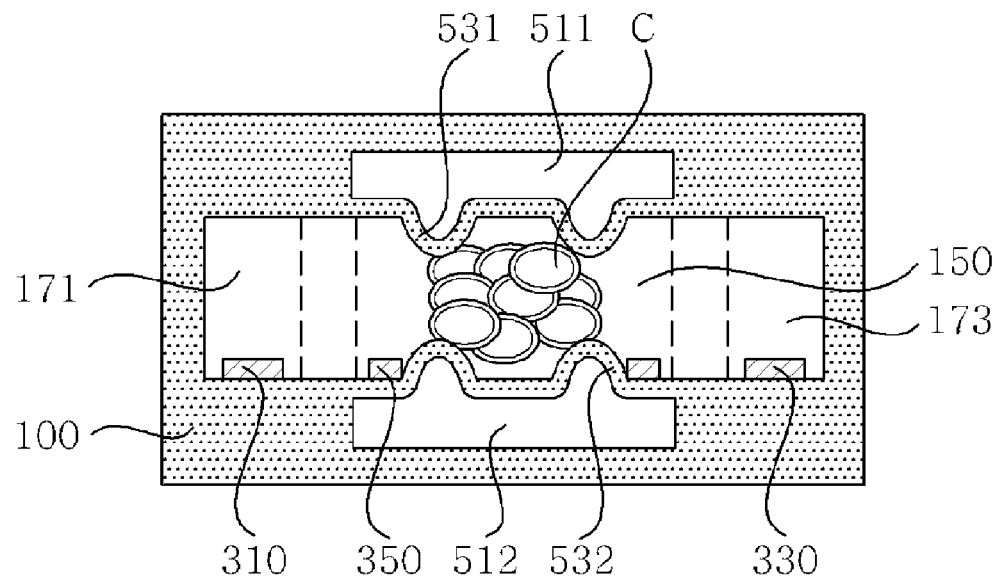
Figure 20:
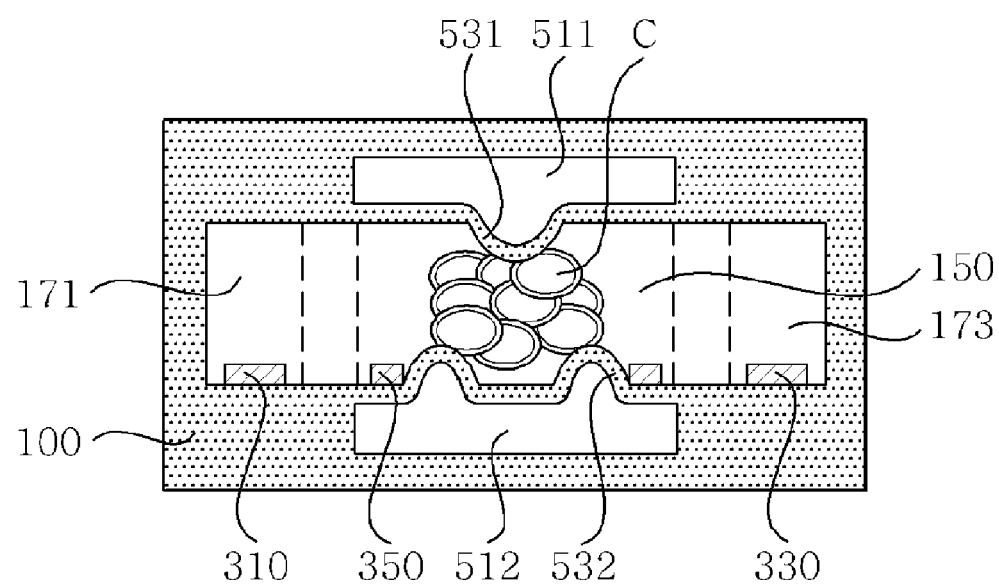

The shape of the membrane 530 is not limited. The shape of the membrane actuating channel 510 influences the shape of the membrane 530. The membrane 530 may be formed in a circular shape, as shown in FIG. 16, a polygonal shape, as shown in FIG. 17, or a ring shape, as shown in FIGS. 18 and 19. Further, as shown in FIG. 20, the shapes of the membrane 530 formed in the upper portion of the well 100 and the membrane 530 formed in the lower portion of the well 100 may be different from each other.

Figure 21:
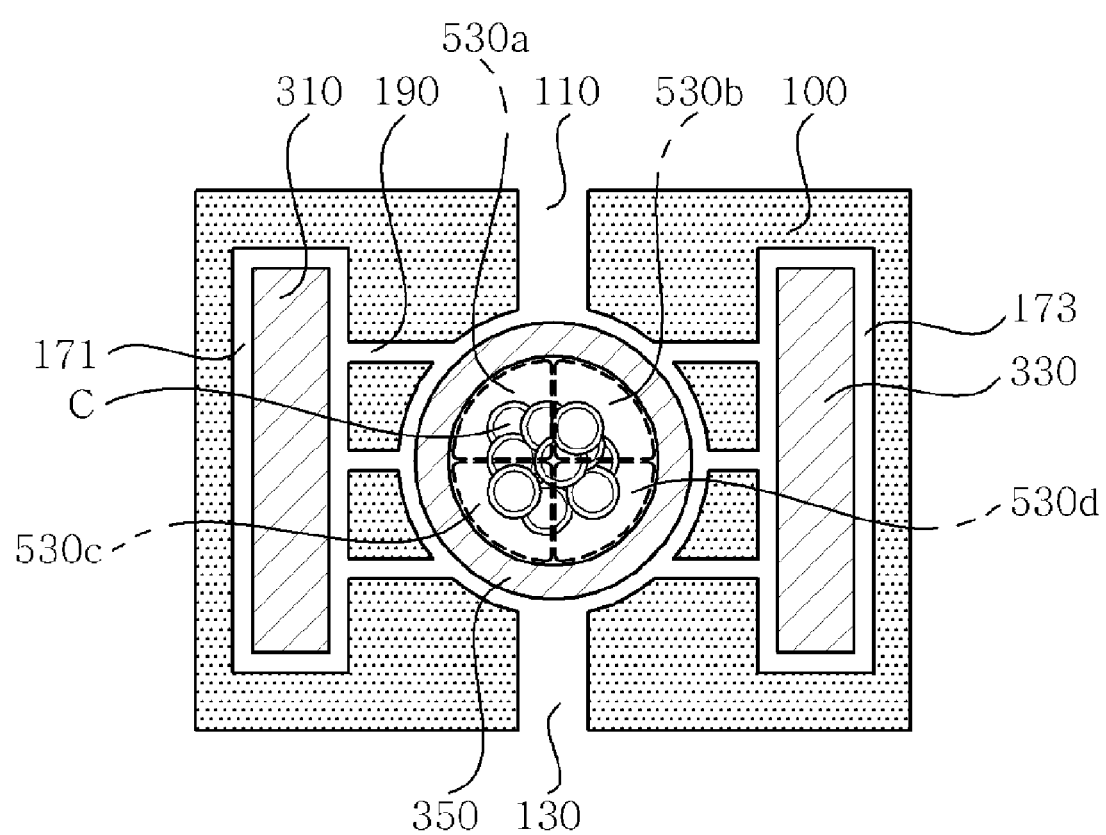

Meanwhile, as shown in FIG. 21, the membrane 530 may be composed of a plurality of membrane units 530a, 530b, 530c and 530d which are independently or dependently actuated. In order for the respective membrane units 530a, 530b, 530c and 530d to be independently actuated, membrane actuating channels 510 corresponding to the respective membrane units 530a, 530b, 530c and 530d must be independently provided. In the case where the membrane 530 is composed of the plurality of membrane units 530a, 530b, 530c and 530d, the mechanical properties of cells can be precisely measured and a variety of types of mechanical stimulation may be applied, compared to the case where one membrane 530 is used.

An optical property measurement unit 700 is a component arranged outside the well 100, or arranged in the cell accommodation unit 150 of the cell 100, and configured to measure the optical properties of cells and/or apply optical stimulation to the cells. The optical property measurement unit 700 is capable of applying optical stimulation, in which wavelength, light quantity or a combination thereof is adjusted, to the cells, and/or measuring the optical properties of the cells. Since the optical property measurement unit 700 is implemented by well-known technologies, a detailed description of the detailed construction thereof is omitted here.

A circuit unit 900 is a component arranged outside the well 100 and configured to control the electrical property measurement unit, the mechanical property measurement unit, and/or the optical property measurement unit, and to analyze and measure the properties of the cells accommodated in the cell accommodation unit 150 according to signals detected by the electrical property measurement unit, the mechanical property measurement unit and/or the optical property measurement unit. For example, the circuit unit 900 may be a specified electronic device or computer.

It is possible to use the above-described cell property measurement device as an independent unit, but it is preferable to implement a system for measuring the properties of cells by connecting a plurality of cell property measurement devices. That is, a cell property measurement system characterized by a plurality of cell property measurement devices being connected in series or parallel or through a combination of series and parallel connections may be used.

Figure 22:
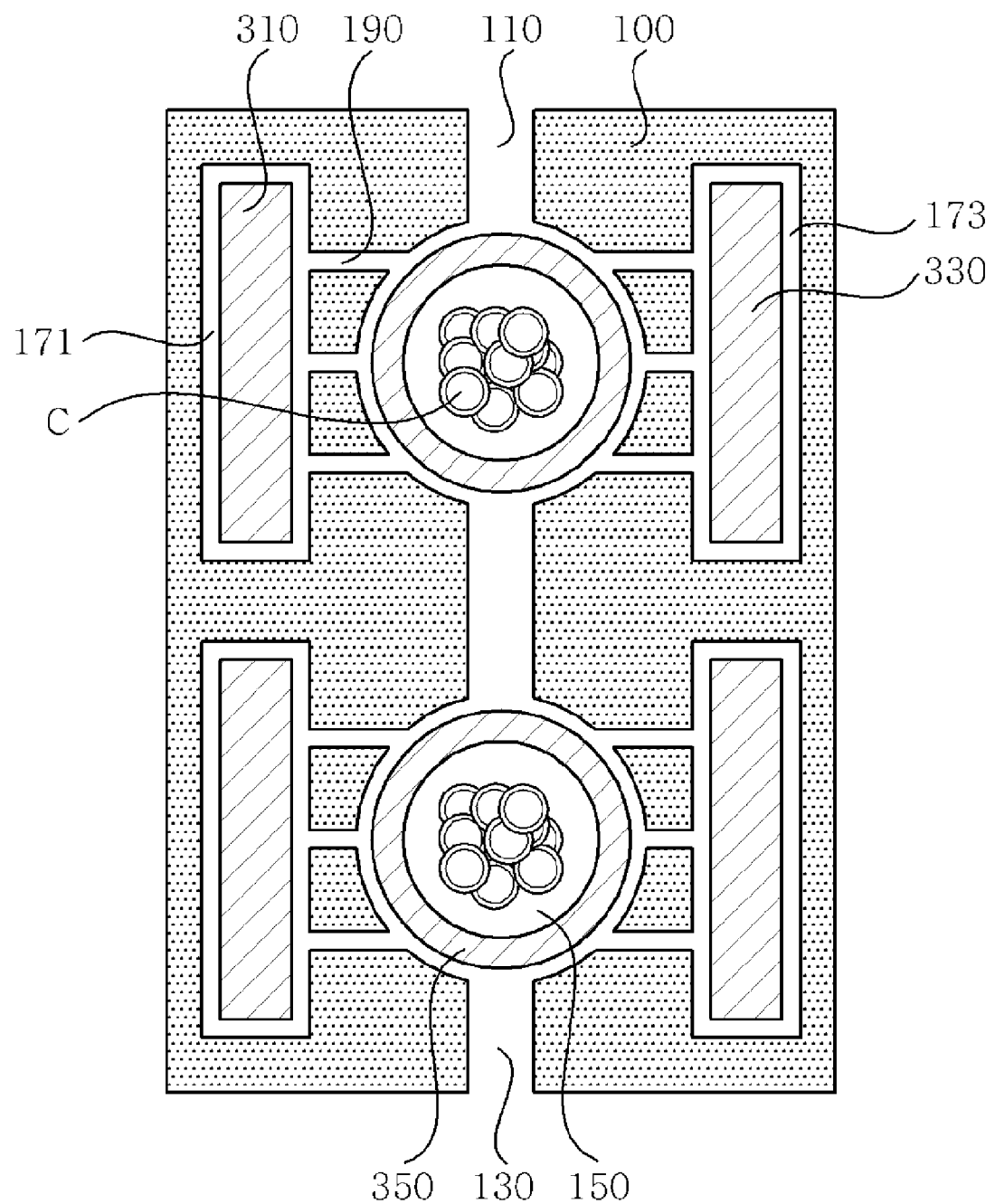
FIGS. 22 to 24 are views showing a system for measuring the properties of cells in which a plurality of cell property measurement devices is connected in a variety of connective shapes.
Figure 23:
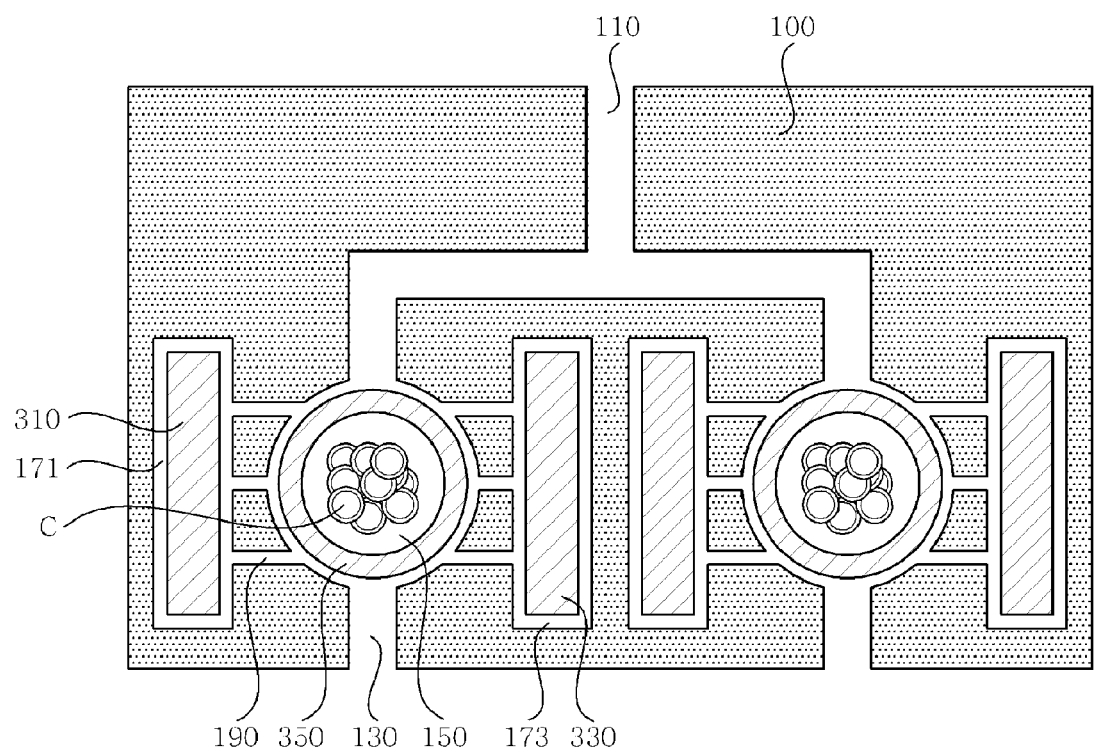
Figure 24:
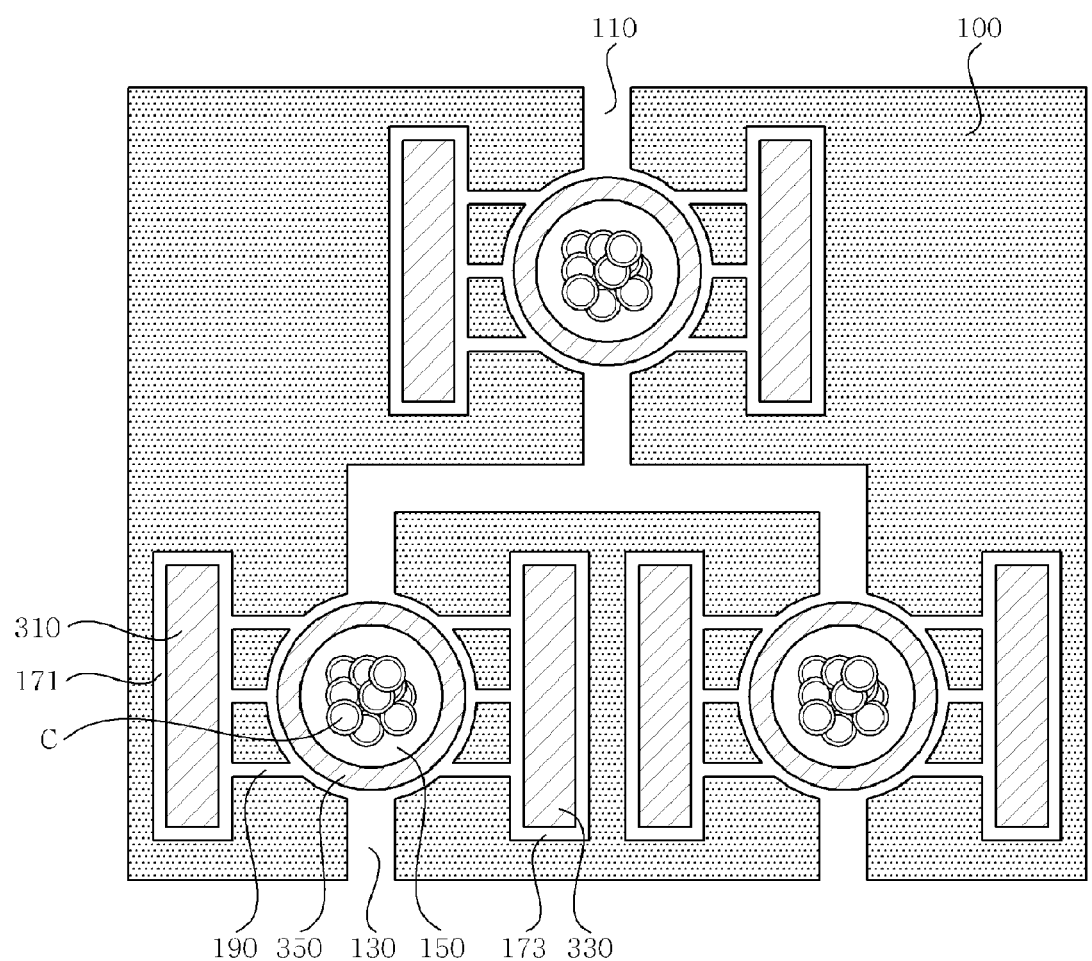

FIG. 22 illustrates a cell property measurement system in which the outlet 130 of one cell property measurement device is connected in series with the inlet 110 of the other cell property measurement device, and FIG. 23 illustrates a cell property measurement system in which the inlets 110 of a plurality of cell property measurement devices are connected in parallel. In addition, as shown in FIG. 24, it is also possible to implement a cell property measurement system by combining and connecting cell property measurement devices in series or parallel.

In the case of a cell property measurement system including a plurality of cell property measurement devices, the connective shape of the first electrodes 310 and the second electrodes 330 included in the respective cell property measurement devices may also be implemented using a variety of different methods. That is, it is possible to individually supply power to the electrodes 310 and 330 included in the plurality of cell property measurement devices, but the cell property measurement system may be constructed such that the first electrodes 310 or the second electrodes 330 are connected in series or parallel.

Figure 25:
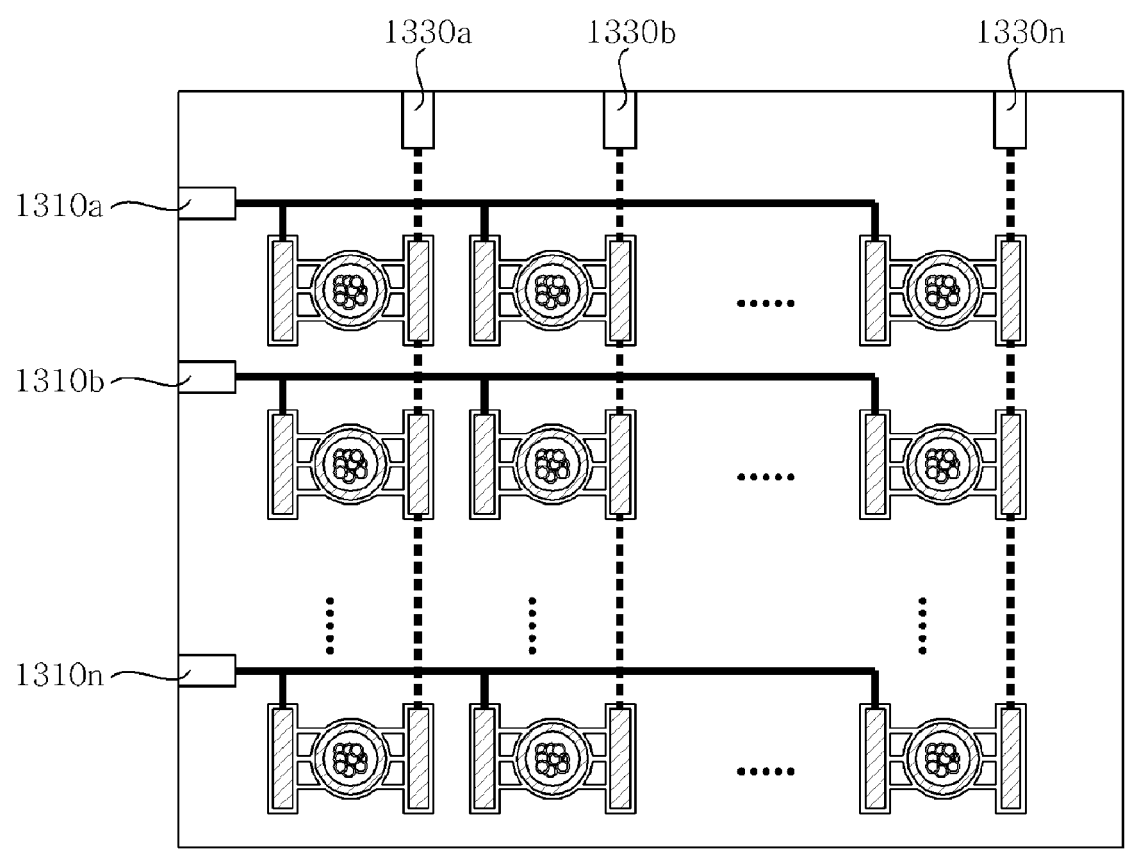
FIGS. 25 and 26 are views illustrating the connective shapes of first and second electrodes.
Figure 26:
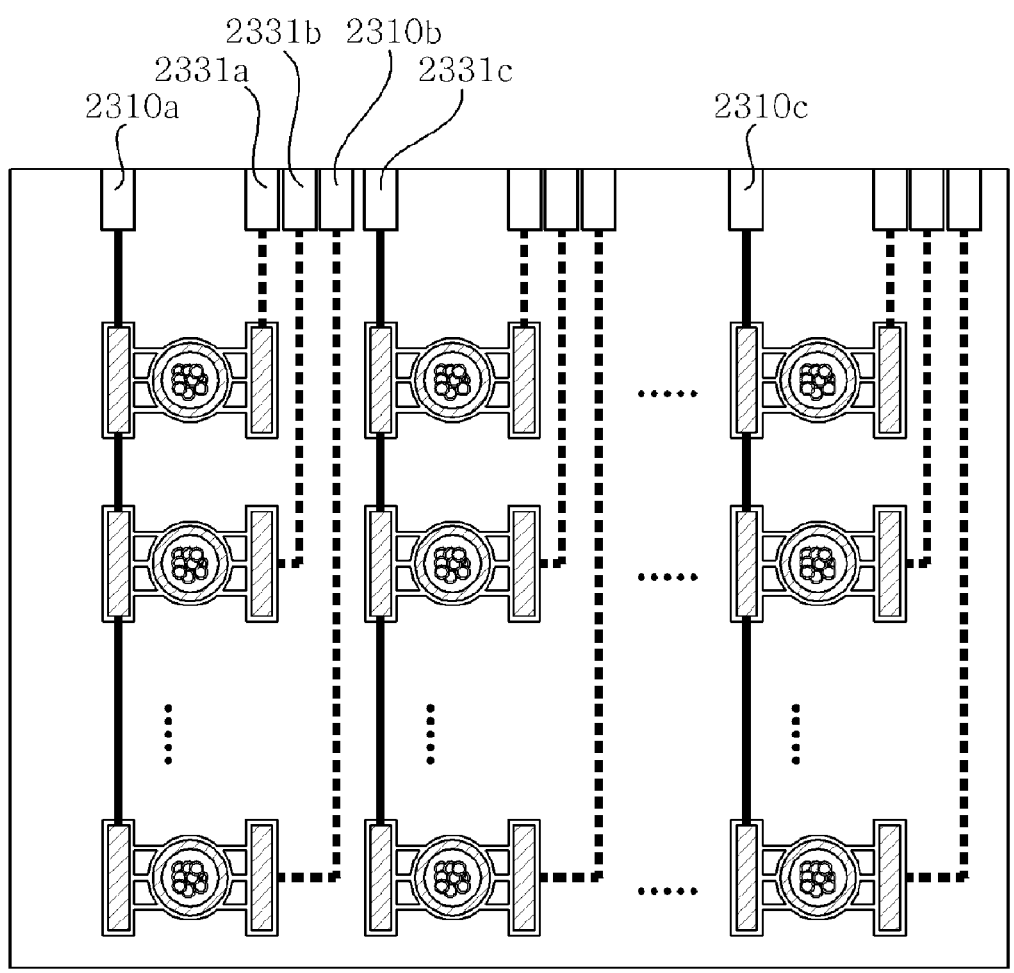

FIG. 25 illustrates a matrix connective shape in which a plurality of first electrodes 310 is connected in common to powers 1310a, 1310b, ..., 1310n arranged in respective rows, and a plurality of second electrodes 330 is connected in common to powers 1330a, 1330b, ..., 1330n arranged in respective columns. FIG. 26 illustrates an individual connective shape in which a plurality of first electrodes 310 is connected in series with powers 2310a, 2310b, ..., 2310n arranged in respective columns, and a plurality of second electrodes 330 is connected to respective separate powers. In addition, although not shown in the drawings, it is possible to construct both the first electrodes 310 and the second electrodes 330 in an individual connective shape, or to individually connect the first electrodes 310 and connect the second electrodes 330 in a common connective shape.

According to the above-described cell property measurement device and cell property measurement system, since the cell accommodation unit 150 having a volume is provided, the properties of three-dimensional cells can be measured.

Further, since electrical, mechanical or optical types of stimulation can be applied to cells using a variety of methods, there is an advantage in that the properties of the cells can be measured in a variety of different ways.

Hereinafter, with reference to FIGS. 27 to 36, a method of measuring the properties of cells according to an embodiment of the present invention will be described in detail.

First, a cell property measurement device, including the cell accommodation unit 150 connected to the inlet 110 and the outlet 130 and configured to accommodate cells and have a volume, the electrical property measurement unit, the mechanical property measurement unit, and/or the optical property measurement unit 700, is provided. The construction of the cell property measurement device is identical to that of the above description, and thus a detailed description thereof is omitted here.

Next, cells are supplied into the cell accommodation unit 150 of the cell property measurement device. After the cells have been supplied into the cell accommodation unit 150, the cells may be cultured and an aggregate of cells may be formed. At this time, an environment required to culture the cells may be created in such a way as to charge a $CO_2$ gas in the membrane actuating channel 510 and to adjust the pH within the well 100 or adjust the distribution of the partial pressure of the gas. In this case, the membrane 530 is made of a gas-permeable material.

Next, the mechanical properties, electrical properties and/or optical properties of the cells are collectively measured. Measuring the properties of the cells may be implemented using a passive measurement method which measures the properties of cells without applying external stimulation to the cells, and an active measurement method which applies external stimulation to cells and measures the properties of the cells acting in response to the stimulation.

In this embodiment, the active measurement method which applies mechanical, electrical or optical stimulation or a combination thereof to the cells and measures the properties of the cells acting in response to the stimulation will be described in detail. The passive measurement method will be understood as a method of removing the application of stimulation from the active measurement method.

Electrical stimulation may be Direct Current (DC) stimulation, Alternating Current (AC) stimulation or a combination thereof, and items for electrical property measurement may include, for example, resistance, capacitance or impedance. The cell property measurement device used in the present embodiment includes the first electrode accommodation unit 171 and the second electrode accommodation unit 173 arranged with the cell accommodation unit 150 disposed therebetween. At this time, the electrical property measurement unit includes the first electrode 310 formed in the first electrode accommodation unit 171 and the second electrode 330 formed in the second electrode accommodation unit 173 so as to measure the electrical properties of the cells accommodated in the cell accommodation unit 150 and/or to apply electrical stimulation to the cells.

Figure 27:
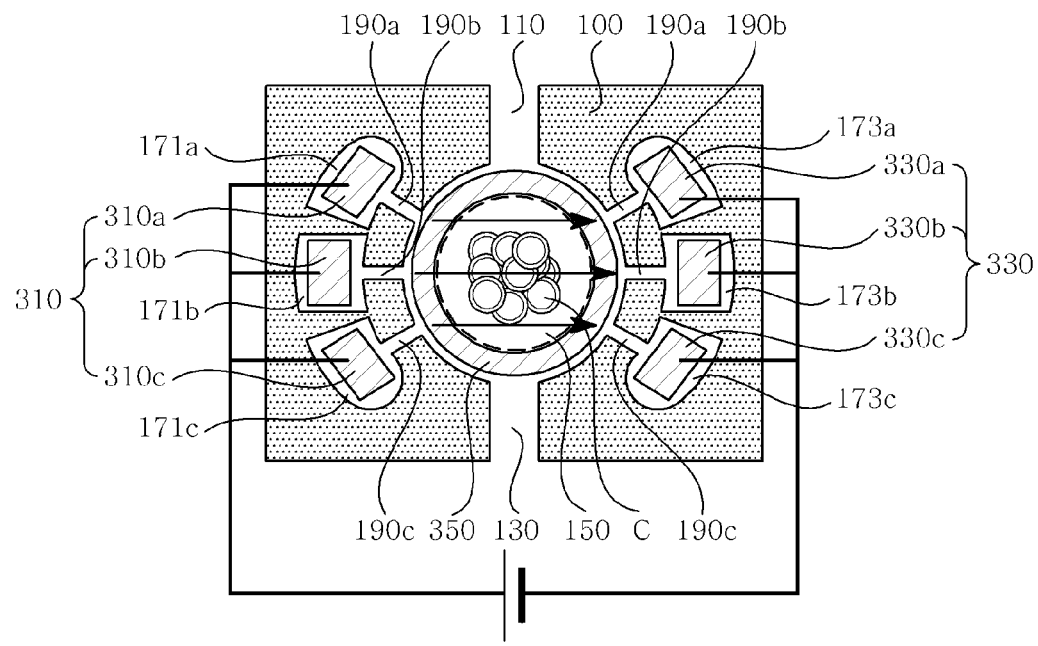
FIGS. 27 to 30 are views showing various embodiments of the application of electrical stimulation to cells.
Figure 28:
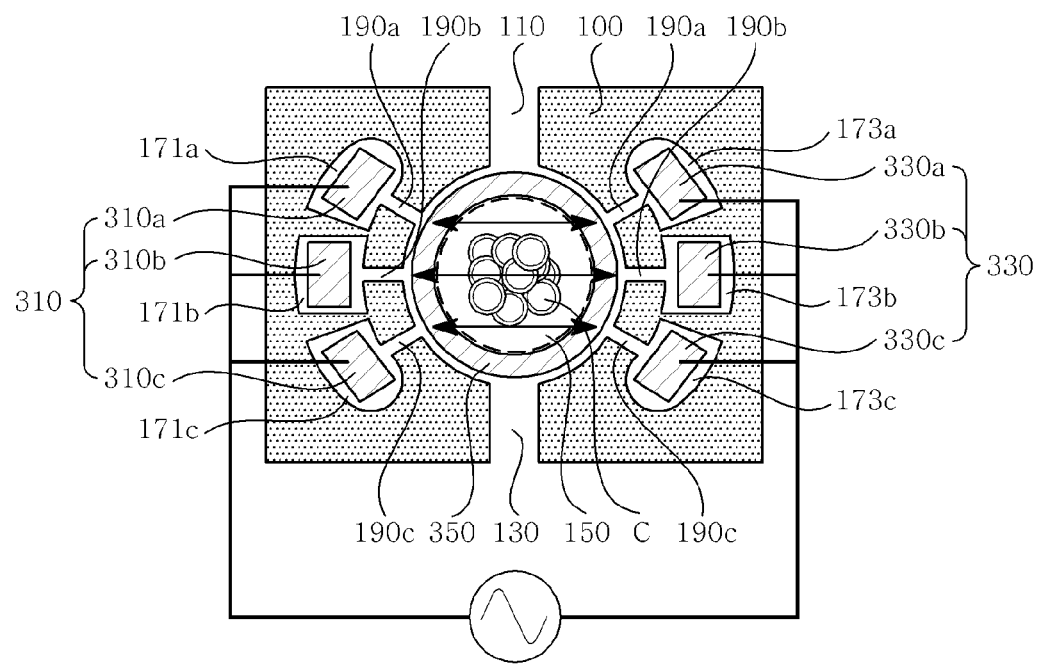

Therefore, electrical stimulation may be applied to the cells in such a way as to form an electric field in the cell accommodation unit 150 by applying, for example, positive polarity to the first electrode 310 and negative polarity to the second electrode 330. In this case, power may be DC power, as shown in FIG. 27, or AC power, as shown in FIG. 28.

Figure 29:
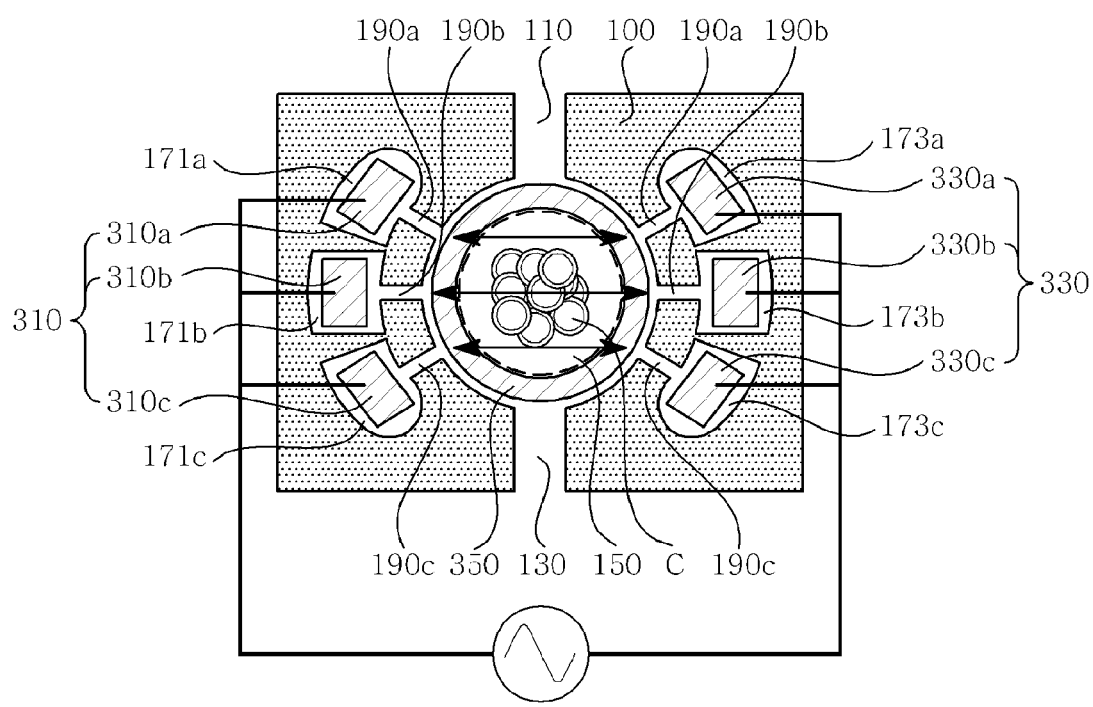
Figure 30:
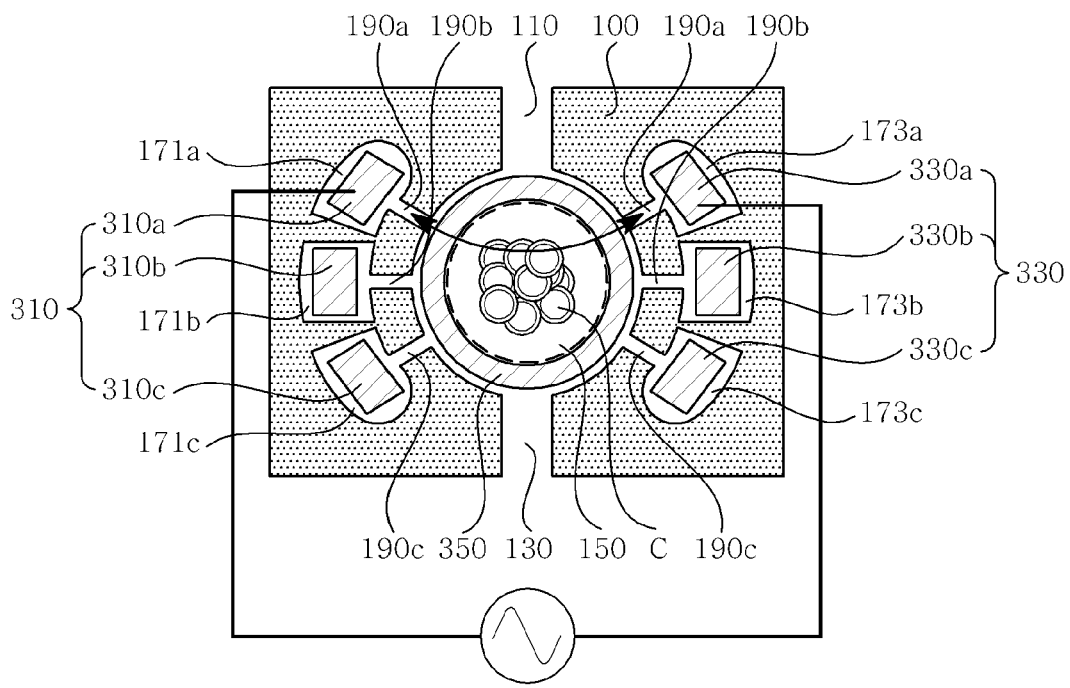

In this case, when the first electrode 310 is composed of a plurality of first electrode units 310a, 310b and 310c and the second electrode 330 is composed of a plurality of second electrode units 330a, 330b and 330c, a variety of types of electrical stimulation may be applied using a method of applying common power to the electrode units, as shown in FIG. 29, or a method of individually applying power to the electrode units, as shown in FIG. 30.

Meanwhile, it can be understood that, when the electrical stimulation application method is inversely used, the electrical properties of cells can be measured by detecting the difference between potentials applied to the electrodes 310 and 330.

Mechanical stimulation may be static or dynamic stimulation, and items for mechanical property measurement may include, for example, stiffness, deformability, or a Poisson ratio. The mechanical property measurement unit according to the present embodiment includes the membrane actuating channel 510 formed either above or below or both above and below the cell accommodation unit 150, and the membrane 530 disposed between the membrane actuating channel 510 and the cell accommodation unit 150 so as to isolate the membrane actuating channel 510 from the cell accommodation unit 150.

Figure 31:
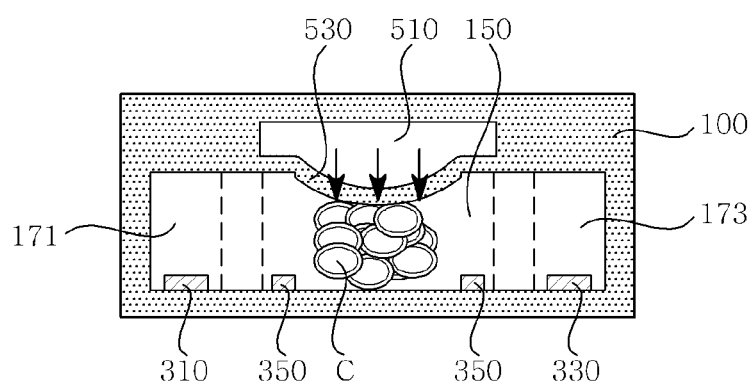
FIGS. 31 to 34 are views showing various embodiments of the application of mechanical stimulation to cells.
Figure 32:
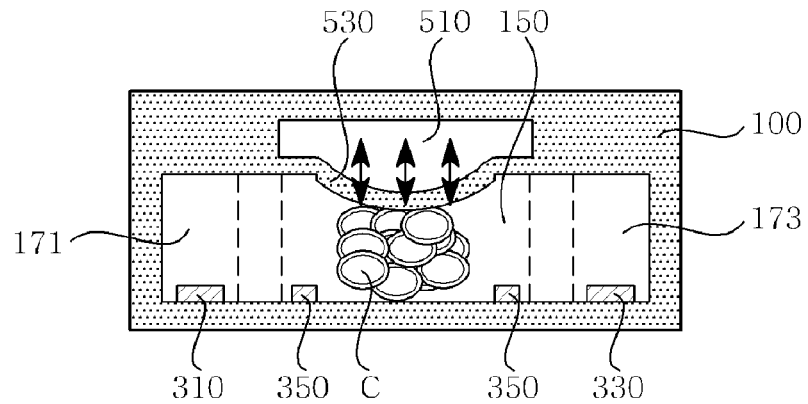

Therefore, mechanical stimulation may be applied to the cells in such a way as to elastically deform the membrane 530 by adjusting the internal pressure of the membrane actuating channel 510. In this case, a method of applying static mechanical stimulation to cells while maintaining the pressure of the membrane actuating channel 510, as shown in FIG. 31, or a method of applying dynamic mechanical stimulation to cells while changing the pressure of the membrane actuating channel 510, as shown in FIG. 32, may be used.

Figure 33:
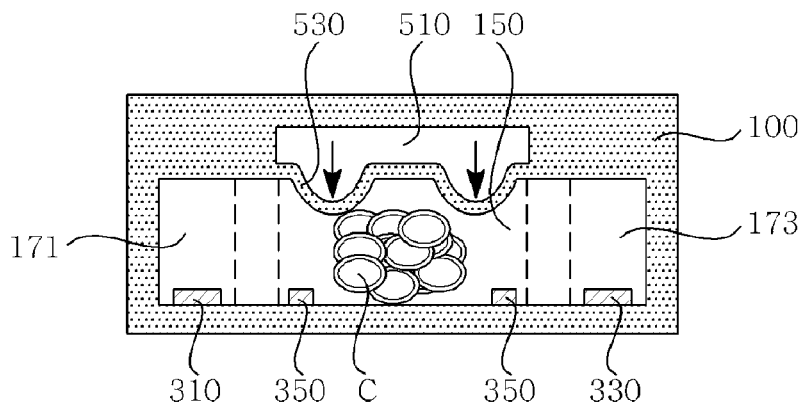
Figure 34:
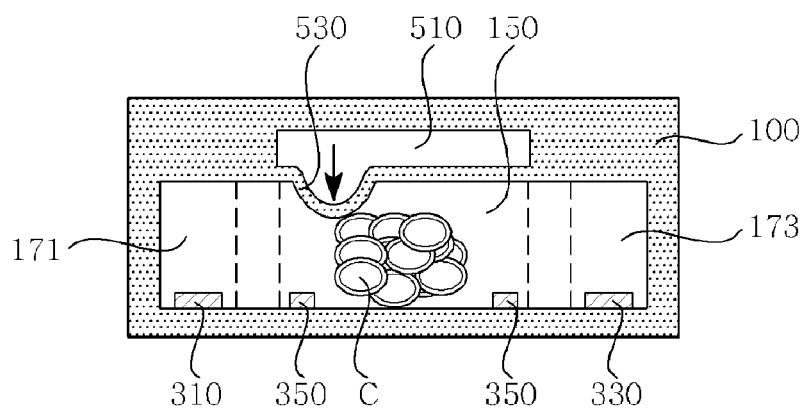

The shape and location of the membrane 530 are changed, or the membrane 530 is composed of a plurality of membrane units 530a, 530b, 530c and 530d which are independently or dependently actuated, and thus a variety of different types of mechanical stimulation may be applied to the cells. FIG. 33 illustrates a common stimulation application method for the membrane 530, which provides the same actuating force to the plurality of membrane units 530a, 530b, 530c and 530d, and FIG. 34 illustrates an individual stimulation application method for the membrane 530, which individually provides actuating forces to the plurality of membrane units 530a, 530b, 530c and 530d.

Meanwhile, it can be understood that, when such a mechanical stimulation application method is inversely used, variation in the pressure applied to the membrane 530 or the pressure of the membrane actuating channel 510 is detected, thus allowing the mechanical properties of the cells to be measured.

Further, even in the measurement of the properties of the cells, it should be noted that a gas required to create an environment for culturing the cells may be injected into the cell accommodation unit 150 through the membrane 530.

Optical stimulation may be static or dynamic stimulation, and items for optical property measurement may include, for example, fluorescence, luminescence, absorbance, the number of cells, or cell size. The optical property measurement unit 700 is a component capable of applying optical stimulation, in which wavelength, light quantity or a combination thereof is adjusted, to cells and/or measuring the optical properties of the cells.

Figure 35:
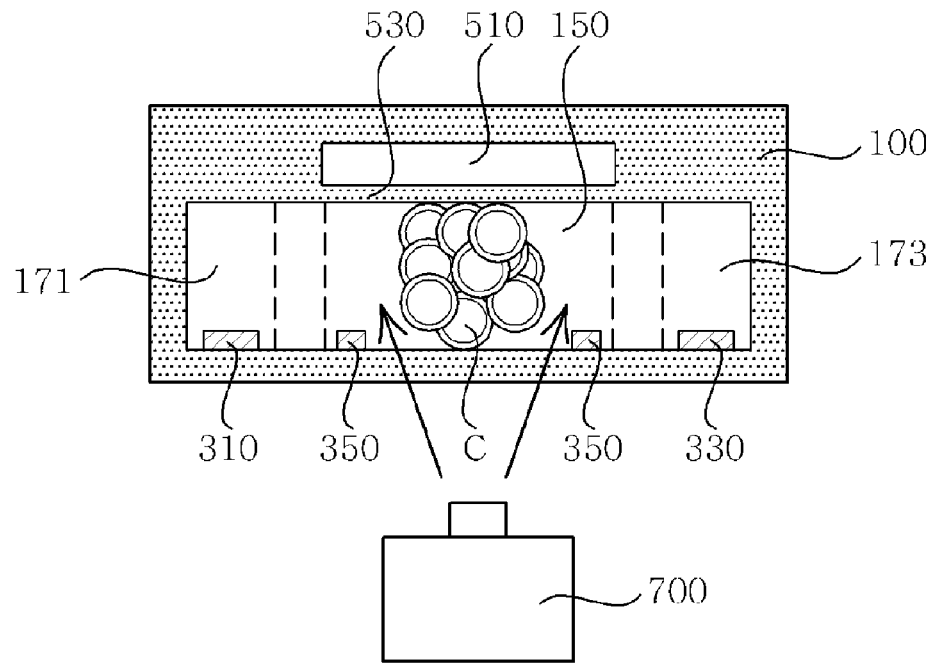
FIGS. 35 and 36 are views showing embodiments of the application of optical stimulation to cells.
Figure 36:
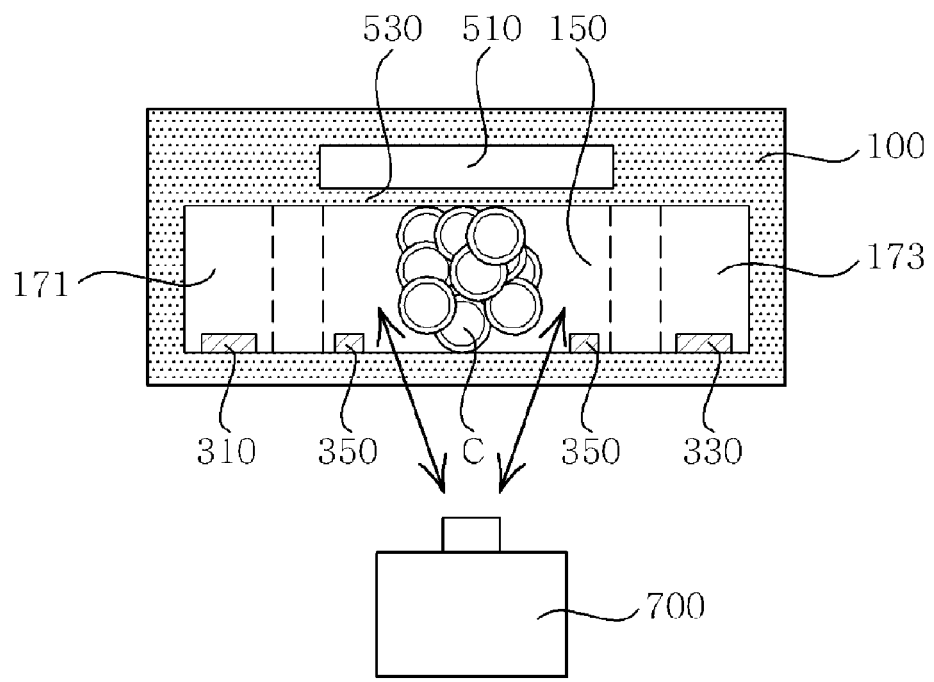

As an optical stimulation application method, a method of applying static stimulation while maintaining the amount of optical stimulation, as shown in FIG. 35, or a method of applying dynamic stimulation while changing the amount of optical stimulation, may be used.

The operation of the above-described electrical property measurement unit, mechanical property measurement unit and/or optical property measurement unit is controlled by the circuit unit 900, and the electrical, mechanical and/or optical properties of cells are measured by the circuit unit 900.

According to the cell property measurement method, there is an advantage in that the electrical, mechanical and/or optical properties of cells acting in response to electrical, mechanical or optical stimulation or a combination thereof can be collectively measured.

As described above, a device and system for measuring the properties of cells according to the present invention are capable of measuring the properties of three-dimensional cells because a cell accommodation unit having a volume is provided.

Further, there is an advantage in that, since electrical, mechanical and optical types of stimulation may be applied to cells using a variety of methods, the properties of cells may be measured in a variety of different ways.

Although the preferred embodiments of the present invention have been disclosed for illustrative purposes, those skilled in the art will appreciate that various modifications, additions and substitutions are possible, without departing from the scope and spirit of the invention as disclosed in the accompanying claims. Accordingly, such modifications, additions and substitutions should also be understood to fall within the scope of the present invention.

What is claimed is:

1. A device for measuring properties of cells, comprising:
a well including a cell accommodation unit connected to an inlet and an outlet, and a first electrode accommodation unit and a second electrode accommodation unit arranged with the cell accommodation unit disposed therebetween;
an electrical property measurement unit including a first electrode formed in the first electrode accommodation unit and a second electrode formed in the second electrode accommodation unit so as to measure electrical properties of cells accommodated in the cell accommodation unit and/or apply electrical stimulation to the cells; and
electric field connection channels formed between the first electrode accommodation unit and the cell accommodation unit and between the second electrode accommodation unit and the cell accommodation unit, and configured to control a pattern of electric fields in the cell accommodation unit in three dimensions by adjusting angles of the electric field connection channels;

wherein the well further includes a mechanical property measurement unit arranged either above or below or both above and below the cell accommodation unit and configured to measure mechanical properties of the cells and/or to apply mechanical stimulation to the cells.

2. The device as set forth in claim 1, wherein the first electrode and the second electrode are arranged symmetrically or asymmetrically with respect to the cell accommodation unit.

3. The device as set forth in claim 1, wherein the first electrode includes a plurality of first electrode units and the second electrode includes a plurality of second electrode units.

4. The device as set forth in claim 1, wherein each of the first electrode and the second electrode has a polygonal shape or an arc shape.

5. The device as set forth in claim 1, further comprising a ground electrode formed in the cell accommodation unit.

6. The device as set forth in claim 1, wherein each of the first electrode accommodation unit and the second electrode accommodation unit includes a plurality of divided spaces.

7. The device as set forth in claim 1, wherein:
the mechanical property measurement unit includes a membrane actuating channel formed either above or below or both above and below the cell accommodation unit of the well and a membrane arranged between the membrane actuating channel and the cell accommodation unit so as to isolate the membrane actuating channel from the cell accommodation unit; and
the membrane is made of an elastically deformable material.

8. The device as set forth in claim 1, further comprising an optical property measurement unit arranged outside the well or arranged in the cell accommodation unit of the well and configured to measure optical properties of the cells and/or to apply optical stimulation to the cells.

9. The device as set forth in claim 7, wherein the membrane includes a plurality of membrane units that are independently or dependently actuated.

10. The device as set forth in claim 8, further comprising a circuit unit arranged outside the well and configured to control the electrical property measurement unit, the mechanical property measurement unit and the optical property measurement unit and to measure properties of the cells accommodated in the cell accommodation unit according to signals detected by the electrical property measurement unit, the mechanical property measurement unit and the optical property measurement unit.

11. The device as set forth in claim 10, wherein the membrane is made of a gas-or liquid-permeable material.

12. A system for measuring properties of cells, wherein a plurality of devices for measuring properties of cells, each device being disclosed in claim 1, is connected in series or parallel, or through a combination of series and parallel connections.

13. The system as set forth in claim 12, wherein inlets of the cell property measurement devices are connected in parallel.

14. The system as set forth in claim 12, wherein an outlet of any one of the cell property measurement devices is connected in series with an inlet of another cell property measurement device.

15. The system as set forth in claim 12, wherein first electrodes or second electrodes of the cell property measurement devices are connected in a matrix connective shape or an individual connective shape.

16. A method of measuring properties of cells, comprising:
(A) providing a device for measuring properties of cells, the device including a cell accommodation unit connected to an inlet and an outlet and configured to accommodate cells and have a volume, an electrical property measurement unit, a mechanical property measurement unit, and/or an optical property measurement unit;
(B) supplying cells into the cell accommodation unit of the cell property measurement device; and
(C) collectively measuring mechanical, electrical and/or optical properties of the cells;
wherein the mechanical property measurement unit includes a membrane actuating channel formed either above or below or both above and below the cell accommodation unit and a membrane disposed between the membrane actuating channel and the cell accommodation unit so as to isolate the membrane actuating channel from the cell accommodation unit;
the membrane includes a plurality of membrane units that are independently or dependently actuated; and
the mechanical stimulation is common membrane stimulation applied to the entire membrane, individual membrane stimulation individually applied to respective membrane units, or a combination thereof.

17. The method as set forth in claim 16, further comprising, before (C), applying mechanical stimulation, electrical stimulation, optical stimulation or a combination thereof to the cells accommodated in the cell accommodation unit.

18. The method as set forth in claim 17, wherein the electrical stimulation is Direct Current (DC) stimulation, Alternating Current (AC) stimulation, or a combination thereof, the mechanical stimulation is static or dynamic stimulation, and the optical stimulation is static or dynamic stimulation.

19. The method as set forth in claim 18, wherein the electrical properties include resistance, capacitance or impedance, the mechanical properties include stiffness, deformability or a Poisson ratio, and the optical properties include fluorescence, luminescence, absorbance, number, or size.

20. The method as set forth in claim 19, wherein the electrical property measurement unit is a component including a first electrode formed in a first electrode accommodation unit and a second electrode formed in a second electrode accommodation unit so as to measure electrical properties of the cells accommodated in the cell accommodation unit and/or to apply electrical stimulation to the cells;
the first electrode includes a plurality of first electrode units and the second electrode includes a plurality of second electrode units; and
the electrical stimulation is applied in common to the first electrode or the second electrode, or individually applied to the first electrode units or the second electrode units.

21. The method as set forth in claim 16, wherein the mechanical stimulation is applied in such a way as to elastically deform the membrane by adjusting an internal pressure of the membrane actuating channel.

22. The method as set forth in claim 21, wherein a gas required to create an environment for culturing the cells is injected into the cell accommodation unit through the membrane.

* * * * *